(12) United States Patent
Hill et al.

(10) Patent No.: US 8,198,401 B2
(45) Date of Patent: Jun. 12, 2012

(54) PEPTIDES ASSOCIATED WITH HLA-DR MHC CLASS II MOLECULE AND INVOLVED IN RHEUMATOID ARTHRITIS

(75) Inventors: Jonathan Hill, London (CA); Ewa Cairns, London (CA); David Bell, London (CA)

(73) Assignee: London Health Sciences Centre Research Inc., London, Ontario (CA)

( * ) Notice: Subject to any disclaimer, the term of this patent is extended or adjusted under 35 U.S.C. 154(b) by 2237 days.

(21) Appl. No.: 10/794,227

(22) Filed: Mar. 5, 2004

(65) Prior Publication Data

US 2009/0010943 A1    Jan. 8, 2009

Related U.S. Application Data

(60) Provisional application No. 60/452,522, filed on Mar. 7, 2003.

(51) Int. Cl.
*A61K 38/00* (2006.01)
*C07K 2/00* (2006.01)
(52) U.S. Cl. .......................... 530/300; 435/810; 514/825
(58) Field of Classification Search .................. None
See application file for complete search history.

(56) References Cited

U.S. PATENT DOCUMENTS 4,281,061 A * 7/1981 Zuk et al. ....................... 435/7.9

OTHER PUBLICATIONS

Menard, H.A., et al. Arthritis Res. 2000;2:429-432.*
S. Bas et al.; Association of rheumatoid factors and anti-filaggrin antibodies with severity of erosions in rheumatoid arthritis; Rheumatology 2000; vol. 39; pp. 1082-1088; British Society for Rheumatology.
Henri A. Menard et al.; Insights into rheumatoid arthritis derived from the Sa immune system; Arthritis Research; published Aug. 17, 2000; vol. 2, No. 6; pp. 429-432; http://arthritis-research.com/content/2/6/429.
Walther J van Venrooij et al.; Citrullination: a small change for a protein with great consequences for rheumatoid arthritis; Arthritis Research; published May 24, 2000; vol. 2, No. 4; pp. 249-251; http://arthritis-research.com/content/2/4/249.
Zhijie Zhou, MD, et al.; Autoantigenic posttranslational modifications of proteins: does it apply to rheumatoid arthritis?; ISSN 1040-8711; pp. 250-253; 2002 Lippincott Williams & Wilkins, Inc.

Christine Masson-Bessiere et al.; The Major Synovial Targets of the Rheumatoid Arthritis-Specific Antifilaggrin Autoantibodies Are Deiminated Forms of the a- and B-Chains of Fibrin; The Journal of Immunology; 2001; vol. 166; pp. 4177-4184; The American Association of Immunologists.
Raphaela Goldbach-Mansky et al.; Rheumatoid arthritis associated autoantibodies in patients with synovitis of recent onset; Arthritis Research; published Mar. 31, 2000, vol. 2, No. 3; pp. 236-243; http://arthritis-research.com/content/2/3/236.
Hill et al., "Cutting Edge: The Conversion of Arginine to Citrulline Allows for a High-Affinity Peptide Interaction with the Rheumatoid Arthritis-Associated HLA-DRB1 *0401 MHC Class II Molecule," *J. Immunol.*, 2003, 171: 538-541.
Ito et al., "HLA-DR4-IE Chimeric Class II Transgenic, Murine Class II-Deficient Mice Are Susceptible to Experimental Allergic Encephalomyelitis," *J. Exp. Med.*, 1996, 183: 2635-2644.
Van Venrooij et al., "Citrullination: a small change for a protein with great consequences for rheumatoid arthritis," *Arthritis Res.*, 2000, 2: 249-251.
James, et al., "HLA-DR1001 Presents 'Altered-Self' Peptides Derived From Joint-Associated Proteins by Accepting Citrulline in Three of Its Binding Pockets," Arthritis & Rheumatism (2010), 62 (10): 2909-2918.
Supplementary Tables 1-3 (pp. 1-4) for James, et al., "HLA-DR1001 Presents 'Altered-Self' Peptides Derived From Joint-Associated Proteins by Accepting Citrulline in Three of Its Binding Pockets," Arthritis & Rheumatism (2010), 62 (10): 2909-2918.
Hagiwara et al., "Deimination of Arginine Residues in Nucleophosmin/B23 and Histones in HL-60 Granulocytes," *Biochem. Biophys. Res. Commun.*, 2002, 290(3): 979-983.
Inagaki et al., "$Ca^{2+}$- dependent Deimination-induced Disassembly of Intermediate Filaments Involves Specific Modification of the Amino-terminal Head Domain," *J. Biol. Chem.*, 1989, 264(30): 18119-18127.
Schellekens et al., "Citrulline is an Essential Constituent of Antigenic Determinants Recognized by Rheumatoid Arthritis-specific Autoantibodies," *J. Clin. Invest.*, 1998, 101(1): 273-281.
Tranquill et al., "Enhanced T Cell Responsiveness to Citrulline-containing Myelin Basic Protein in Multiple Sclerosis Patients," *Mult. Scler.*, 2000, 6(4): 220-225.

* cited by examiner

*Primary Examiner* — Gerald R Ewoldt
(74) *Attorney, Agent, or Firm* — Knobbe Martens Olson & Bear LLP

(57) ABSTRACT

Antigenic peptides that bind to MHC Class II molecules with the shared epitope referred to as HLA-DR molecules are disclosed. More specifically, are citrullinated antigenic peptides having an increased affinity for HLA-DR molecules and associated with Rheumatoid Arthritis. These novel peptides provide the basis for new methods of diagnosis and treatment of Rheumatoid Arthritis.

6 Claims, 7 Drawing Sheets

US 8,198,401 B2

PEPTIDES ASSOCIATED WITH HLA-DR MHC CLASS II MOLECULE AND INVOLVED IN RHEUMATOID ARTHRITIS

This application claims priority to U.S. provisional patent application Ser. No. 60/452,522 filed on Mar. 7, 2003, which is hereby incorporated by reference in its entirety.

This application incorporates by reference the sequence listing submitted as an ASCII text file via EFS-Web on Nov. 14, 2011. The Sequence Listing is provided as a file entitled SIMMC68003AUSSequenceListing.txt created on Nov. 14, 2011, which is 16 Kb in size.

FIELD OF THE INVENTION

The invention relates to novel antigenic peptides that bind to MHC Class II molecules with the shared epitope referred to as HLA-DR molecules. More specifically, the invention is directed to citrullinated antigenic peptides that have an increased affinity for HLA-DR molecules and are associated with Rheumatoid Arthritis. As such these novel peptides provide the basis for new methods of diagnosis and treatment of Rheumatoid Arthritis.

BACKGROUND OF THE INVENTION

Throughout this application, various references are cited in parentheses to describe more fully the state of the art to which this invention pertains. The disclosure of these references are hereby incorporated by reference into the present disclosure.

Rheumatoid arthritis (RA) is a prevalent autoimmune disease characterized by synovial inflammation and pannus formation which can lead to cartilage and bone degradation. Genetic susceptibility to this disease is associated with MHC class II molecules that contain an amino acid motif known as the shared epitope (SE) and are designated as HLA-DR molecules (Gregersen, P. K., J. Silver, R. J. Winchester. 1987. The shared epitope hypothesis. An approach to understanding the molecular genetics of susceptibility to rheumatoid arthritis. *Arthritis Rheum.* 30:1205, Zhou, Z., H. A. Menard. 2002. Autoantigenic posttranslational modifications of proteins: does it apply to rheumatoid arthritis? *Curr. Opin. Rheumatol.* 14:250). The shared epitope, expressed by the amino acid residues Q/R, K/R, R, A, A, is positively charged and forms one of the major peptide anchoring pockets (known as P4) of the MHC class II molecules.

Previous reports have suggested that a distinct feature of a putative pathogenic peptide involved in RA may be the presence of the negatively charged side-chain at P4 (interacting with the shared epitope) (Hammer J., Gallazzi F., Bono E., Karr R. W., Guenot J., Valsasnini P., Nagy Z. A., Sinigaglia F. 1995. Peptide binding specificity of HLA-DR4 molecules: correlation with rheumatoid arthritis association. *J. Exp. Med.* 181:1847). This is based on the fact that certain MHC class II molecules, HLA-DR*0401 and HLA-DR*0404 (allelic variants) have a substantially higher affinity for aspartic and glutamic acid amino acid residues at the P4 pocket than the RA non-associated HLA-DR*0402 molecule. However, after analysis of multiple DRB1 pocket profiles it can be found that some RA non-associated alleles have a higher affinity for negatively charged amino acids at their P4 pockets than even HLA-DR*0101, HLA-DR*0401, and HLA-DR*0404, such as HLA-DR*0301 (Sturniolo T, Bono E, Ding J, Raddrizzani L, Tuereci O, Sahin U, Braxenthaler M, Gallazzi F, Protti M P, Sinigaglia F, Hammer J. 1999. Generation of tissue-specific and promiscuous HLA ligand databases using DNA microarrays and virtual HLA class II matrices. *Nat. Biotechnol.* 17:555). Some MHC molecules appear to be protective against disease (e.g. HLA-DR*0402), rather than simply non-associated, suggesting that a passive role for these alleles in peptide binding may not occur (Reviron, D., A. Perdriger, E. Toussirot, D. Wendling, N. Balandraud, S. Guis, G. Semana, P. Tiberghien, P. Mercier, J. Roudier. 2001. Influence of shared epitope-negative HLA-DRB1 alleles on genetic susceptibility to rheumatoid arthritis. *Arthritis Rheum.* 44:535). Instead, protective alleles may bind a putative pathogenic peptide with high enough affinity as to induce negative selection, or to establish peripheral tolerance.

The MHC class II molecules with the shared epitope may participate in disease pathogenesis by selectively binding arthritogenic peptides for presentation to autoreactive $CD4^+$ T cells. Currently, the nature of the autoantigen responsible for RA is not known. While many candidate autoantigens have been investigated in the context of RA associated MHC, a common disease specific target of the $CD4^+$ T cell and B cell immune response remains elusive. Recent studies have shown that RA patients have a subset of IgG autoantibodies that are both sensitive and specific (>90%) for the diagnosis of RA. The target of these autoantibodies is citrulline, a post-translationally modified arginine (deiminated arginine) found within the context of certain protein/peptide sequences (van Venrooij, W. J., G. J. Pruijn. 2000. Citrullination: a small change for a protein with great consequences for rheumatoid arthritis. *Arthritis Res.* 2:249). Citrulline is the essential antigenic epitope target of anti-perinuclear, anti-keratin, anti-filaggrin, anti-cyclic citrullinated peptide, and anti-Sa antibodies (van Venrooij, W. J., G. J. Pruijn. 2000. Citrullination: a small change for a protein with great consequences for rheumatoid arthritis. *Arthritis Res.* 2:249; Zhou, Z., H. A. Menard. 2002. Autoantigenic posttranslational modifications of proteins: does it apply to rheumatoid arthritis? *Curr. Opin. Rheumatol.* 14:250). These antibodies target citrulline within a number of different proteins, the joint derived targets appears to be vimentin and fibrin(ogen) (Menard, H. A., E. Lapointe, M. D. Rochdi, Z. J. Zhou. 2000. Insights into rheumatoid arthritis derived from the Sa immune system. *Arthritis Res.* 2:429; Christine Masson-Bessiere et al., 2001. The Major Synovial Targets of the Rheumatoid Arthritis-Specific Antifilaggrin Autoantibodies Are Deiminated Forms of the ↦and ⳨Chains of Fibrin 1 *The Journal of Immunology* 166: 4177-4184). It is also observed that anti-citrulline antibody production is significantly associated with the presence of the MHC shared epitope in RA patients (Goldbach-Mansky R, Lee J, McCoy A, Hoxworth J, Yarboro C, Smolen J S, Steiner G, Rosen A, Zhang C, Menard H A, Zhou Z J, Palosuo T, Van Venrooij W J, Wilder R L, Klippel J H, Schumacher H R Jr, El-Gabalawy H S. 2000. Rheumatoid arthritis associated autoantibodies in patients with synovitis of recent onset. *Arthritis Res.* 2:236; Bas S, Pemeger T V, Mikhnevitch E, Seitz M, Tiercy J M, Roux-Lombard P, Guerne P A. 2000. Association of rheumatoid factors and anti-filaggrin antibodies with severity of erosions in rheumatoid arthritis. *Rheumatology (Oxford)*. 39:1082).

The Applicant has now demonstrated that a unique interaction exists between the shared epitope of MHC class II molecules and the amino acid citrulline. This interaction is involved in generating T cell responses and subsequently B cell responses to these antigens in RA patients. Furthermore, the Applicant has now identified novel citrullinated antigens that evoke a T cell response leading to inflammation and RA.

SUMMARY OF THE INVENTION

The Applicant has identified novel citrullinated antigens that evoke a T cell response via binding to the positively charged P4 pocket (the shared epitope) of MHC class II molecules. The Applicant has demonstrated that the modification of a positively charged amino acid to that of citrulline, an uncharged polar amino acid, leads to the increased affinity for the antigen to MHC class II molecules with the shared epitope. This increased antigen affinity leads to T cell activation which in turn mediates an inflammatory reaction resulting in the development of an autoimmune disorder, such as Rheumatoid Arthritis, in a subject.

As such, the present invention encompasses the use of the citrullinated peptides of the invention in a variety of diagnostic and therapeutic approaches to diagnose or treat autoimmune disease characterized by the binding of a citrullinated peptide with MHC class II molecules with the shared epitope leading to T cell activation.

The T cell responses to citrulline containing peptides (via conversion of arginine to citrulline, a process which replaces the charged imino side-chain group with an uncharged carbonyl) were studied in HLA-DRB1*0401 transgenic (DR4-IE tg) mice. The work demonstrated that the conversion of arginine to citrulline at the peptide side-chain position interacting with the shared epitope significantly increases peptide-MHC affinity and leads to the activation $CD4^+$ T cells in the DR4-IE tg mice. This post-translational modification was necessary to elicit a CD4+ T cell response to these peptides in DR4-IE tg mice. Peptide affinity for a number of HLA alleles was assessed and showed that only MHC class II molecules with the shared epitope had an increased affinity for a citrulline containing peptide.

Taken together, the Applicant has identified a novel peptide-MHC interaction that helps to explain the molecular basis of disease associated HLA alleles in RA and more specifically reveals that MHC class II molecules with the shared epitope are involved in initiating an autoimmune response to citrullinated self-antigens in RA patients. The invention encompasses all MHC Class II molecules having a shared epitope sequence. Such MHC molecules may include HLA-DRB1*0401, HLA-DRB1*0404, HLA-DRB1*0405, HLA-DRB1*0408, HLA-DRB1*1001, HLA-DRB1*0101, HLA-DRB1*0102 and HLA-DRB1*1402.

With the knowledge that citrullinated peptides act as arthritogenic antigens leading to T cell activation and resultant disease, novel and improved methods for diagnosis of autoimmune disorders, such as RA, involving this activation mechanism are now made available as well as the predisposition to developing such autoimmune disorders including RA, are now made available. Furthermore, novel therapeutic approaches to treat autoimmune disorders including RA are now also made available.

According to an aspect of the invention are novel citrullinated peptides that bind with high affinity to MHC class II molecules with the shared epitope said peptides evoking a T cell response in the blood of a patient with an autoimmune disorder or a patient at risk for developing an autoimmune disorder. The T cell is preferably a CD4+ T cell.

According to another aspect of the invention are novel citrullinated peptides that bind with high affinity to MHC class II molecules with the shared epitope said peptides evoking a T cell response in the blood of a patient with RA, or a patient at risk for developing RA.

According to a further aspect of the invention are novel citrullinated peptides that bind with high affinity to MHC class II molecules with the shared epitope, said peptides evoking a T cell response in the blood of a RA patient, or a patient at risk for developing RA, wherein said T cell is a CD4+ T cell.

According to yet a further aspect of the invention is a novel citrullinated peptide, said peptide being produced by the action of peptidylarginine deiminase on an endogenous or exogenous protein, wherein said citrullinated peptide binds to MHC class II molecules having the shared epitope.

According to yet another aspect of the invention is a citrullinated peptide that binds with high affinity to MHC class II molecules with the shared epitope, said peptide evoking a T cell response in the blood of a RA patient, or a patient at risk for developing RA, said peptide being selected from the group consisting of citrullinated fibrinogen peptides and citrullinated vimentin peptides. In preferred aspects, the fibrinogen and vimentin peptides for use in the invention and the target of citrullination, are selected from the known human sequences for each of these proteins. Furthermore, the fibrinogen human protein sequences may be further selected from alpha/alpha-e chain precursor protein, beta chain precursor protein, alpha-A chain precursor protein and gamma chain precursor protein. In other aspects, the citrullinated peptide may be a full length fibrinogen or vimentin protein. Protein sequences encompassed by the present invention may be found in Genbank and SWISS-PROT as is understood by one of skill in the art.

According to another aspect of the invention is a peptide containing a deiminated arginine, the peptide being from at least about 9 amino acids in length, the peptide binding with high affinity to MHC class II molecules with the shared epitope, wherein the peptide evokes a T cell response in the blood of a RA patient, or a patient at risk for developing RA.

According to still another aspect of the invention is a citrullinated peptide that binds with high affinity to MHC class II molecules with the shared epitope, said peptide evoking a T cell response in the blood of a RA patient, or a patient at risk for developing RA, said peptide comprising at least one of the amino acid sequences selected from the group consisting of: SAVRACitSSVPGVR (SEQ ID NO. 1); FSMCitIVCLV (SEQ ID NO. 2); VVECitHQSAC (SEQ ID NO. 3); FTNCitINKLK (SEQ ID NO. 4); LRSCitIEVLK (SEQ ID NO. 5); VLKCitKVIEK (SEQ ID NO. 6); IKICitSCRGS (SEQ ID NO. 7); LPSCitDRQHL (SEQ ID NO. 8); FRHCitHPDEA (SEQ ID NO. 9); FPSCitGKSSS (SEQ ID NO. 10); IQQCitMDGSL (SEQ ID NO. 11); LTQCitGSVLR (SEQ ID NO. 12); YHFCitVGSEA (SEQ ID NO. 13); YDPCitNNSPY (SEQ ID NO. 14); VSFCitGADYS (SEQ ID NO. 15); YSLCitAVRMK (SEQ ID NO. 16); MKICitPLVTQ (SEQ ID NO. 17); YRACitPAKAA (SEQ ID NO. 18); WQKCitQKQVK (SEQ ID NO. 19); IQNCitQDGSV (SEQ ID NO. 20); WYNCitCHAAN (SEQ ID NO. 21); YSMCitKMSMK (SEQ ID NO. 22); MKICitPFFPQ (SEQ ID NO. 23); LHPCitNLILY (SEQ ID NO. 24); VATCitDNCCI (SEQ ID NO. 25); LDECitFGSYC (SEQ ID NO. 26); LKSCitIMLEE (SEQ ID NO. 27); FQKCitLDGSV (SEQ ID NO. 28); YALCitVELED (SEQ ID NO. 29); WNGCitTSTA (SEQ ID NO. 30); WKTCitWYSMK (SEQ ID NO. 31); YATCitSSAVR (SEQ ID NO. 32); VRLCitSSVPG (SEQ ID NO. 33); LNDCitFANYI (SEQ ID NO. 34); MLQCitEEAEN (SEQ ID NO. 35); LNLCitETNLD (SEQ ID NO. 36); VETCitDGQVI (SEQ ID NO. 37) and functional analogues thereof.

According to still a further aspect of the invention is a citrullinated peptide that binds with high affinity to MHC class II molecules with the shared epitope, said peptide evoking a T cell response in the blood of a RA patient, or a patient at risk for developing RA, said peptide being selected from the group consisting of: SAVRACitSSVPGVR (SEQ ID NO. 1); FSMCitIVCLV (SEQ ID NO. 2); VVECitHQSAC (SEQ ID NO. 3); FTNCitINKLK (SEQ ID NO. 4); LRSCitIEVLK (SEQ ID NO. 5); VLKCitKVIEK (SEQ ID NO. 6); IKICitSCRGS (SEQ ID NO. 7); LPSCitDRQHL (SEQ ID NO. 8); FRHCitHPDEA (SEQ ID NO. 9); FPSCitGKSSS (SEQ ID NO. 10); IQQCitMDGSL (SEQ ID NO. 11); LTQCitGSVLR (SEQ ID NO. 12); YHFCitVGSEA (SEQ ID NO. 13); YDPCitNNSPY (SEQ ID NO. 14); VSFCitGADYS (SEQ ID NO. 15); YSLCitAVRMK (SEQ ID NO. 16); MKICitPLVTQ (SEQ ID NO. 17); YRACitPAKAA (SEQ ID NO. 18); WQKCitQKQVK (SEQ ID NO. 19); IQNCitQDGSV (SEQ ID NO. 20); WYNCitCHAAN (SEQ ID NO. 21); YSMCitKMSMK (SEQ ID NO. 22); MKICitPFFPQ (SEQ ID NO. 23); LHPCitNLILY (SEQ ID NO. 24); VATCitDNCCI (SEQ ID NO. 25); LDECitFGSYC (SEQ ID NO. 26); LKSCitIMLEE (SEQ ID NO. 27); FQKCitLDGSV (SEQ ID NO. 28); YALCitVELED (SEQ ID NO. 29); WNGCitTSTA (SEQ ID NO. 30); WKTCitWYSMK (SEQ ID NO. 31); YATCitSSAVR (SEQ ID NO. 32); VRLCitSSVPG (SEQ ID NO. 33); LNDCitFANYI (SEQ ID NO. 34); MLQCitEEAEN (SEQ ID NO. 35); LNLCitETNLD (SEQ ID NO. 36); VETCitDGQVI (SEQ ID NO. 37) and functional analogues thereof.

Also within the scope of the invention are functional analogues of the peptides of the invention as well as multimers of the peptides according to the invention such as for example a dimer or trimer of the peptides according to the invention. A multimer according to the invention can either be a homomer, consisting of a multitude of the same peptide, or a heteromer consisting of different peptides. The characteristic amino acid sequences of the peptides according to the invention can be flanked by random amino acid sequences. Preferred are flanking sequences, that have a stabilizing effect on the peptides, thus increasing their biological availability.

It is understood by one of skill in the art that certain of the peptide amino acid sequences listed supra have additional arginines within the sequence that may be converted to citrulline.

According to another aspect of the present invention is a composition comprising a citrullinated peptide that binds with high affinity to MHC class II molecules with the shared epitope, and is capable of evoking a T cell response in the blood of a RA patient, or a patient at risk for developing RA and a pharmaceutically acceptable carrier. The citrullinated peptide may be selected from the group consisting of SAVRACitSSVPGVR (SEQ ID NO. 1); FSMCitIVCLV (SEQ ID NO. 2); VVECitHQSAC (SEQ ID NO. 3); FTNCitINKLK (SEQ ID NO. 4); LRSCitIEVLK (SEQ ID NO. 5); VLKCitKVIEK (SEQ ID NO. 6); IKICitSCRGS (SEQ ID NO. 7); LPSCitDRQHL (SEQ ID NO. 8); FRHCitHPDEA (SEQ ID NO. 9); FPSCitGKSSS (SEQ ID NO. 10); IQQCitMDGSL (SEQ ID NO. 11); LTQCitGSVLR (SEQ ID NO. 12); YHFCitVGSEA (SEQ ID NO. 13); YDPCitNNSPY (SEQ ID NO. 14); VSFCitGADYS (SEQ ID NO. 15); YSLCitAVRMK (SEQ ID NO. 16); MKICitPLVTQ (SEQ ID NO. 17); YRACitPAKAA (SEQ ID NO. 18); WQKCitQKQVK (SEQ ID NO. 19); IQNCitQDGSV (SEQ ID NO. 20); WYNCitCHAAN (SEQ ID NO. 21); YSMCitKMSMK (SEQ ID NO. 22); MKICitPFFPQ (SEQ ID NO. 23); LHPCitNLILY (SEQ ID NO. 24); VATCitDNCCI (SEQ ID NO. 25); LDECitFGSYC (SEQ ID NO. 26); LKSCitIMLEE (SEQ ID NO. 27); FQKCitLDGSV (SEQ ID NO. 28); YALCitVELED (SEQ ID NO. 29); WNGCitTSTA (SEQ ID NO. 30); WKTCitWYSMK (SEQ ID NO. 31); YATCitSSAVR (SEQ ID NO. 32); VRLCitSSVPG (SEQ ID NO. 33); LNDCitFANYI (SEQ ID NO. 34); MLQCitEEAEN (SEQ ID NO. 35); LNLCitETNLD (SEQ ID NO. 36); and VETCitDGQVI (SEQ ID NO. 37).

The invention also provides use of the citrullinated peptide antigen for the preparation of a diagnostic means for use in a method of diagnosing an autoimmune disorder such as Rheumatoid Arthritis, or susceptibility to an autoimmune disorder such as Rheumatoid Arthritis, in an individual, the method comprising determining whether T cells of the individual recognize the citrullinated peptide antigen as bound to the MHC class II shared epitope positive cell, wherein recognition by the T cells indicates that the individual has, or is susceptible to, an autoimmune disorder such as Rheumatoid Arthritis.

According to still another aspect of the present invention is a diagnostic method for the detection of autoreactive T cells which are reactive with a citrullinated antigen bound to MHC class II shared epitope positive cell, said method comprising;
  incubating an isolated sample of peripheral blood mononuclear cells from a patient with one or more citrullinated peptide antigens;
  detecting the response of T cells, indicating the presence of activated autoreactive T cells in said patient.

According to another aspect of the present invention is a test kit for the detection of activated autoreactive T cells which are reactive with a citrullinated antigen bound to an MHC class II shared epitope positive cell, said test kit comprising one or more citrullinated antigens.

The invention additionally provides citrullinated peptide antigens, optionally in association with a carrier, for use in a method of treating or preventing Rheumatoid Arthritis, by desensitizing said T cells which recognize the citrullinated peptide antigens.

According to still a further aspect of the present invention is a method for treating a subject suffering from Rheumatoid Arthritis evoked by the binding of a citrullinated peptide to MHC class II molecules with the shared epitope leading to a T cell response, said method comprising;
  administering a T cell tolerance inducing amount of a composition comprising a citrullinated peptide comprising an amino acid sequence selected from the group consisting of: SAVRACitSSVPGVR (SEQ ID NO. 1); FSMCitIVCLV (SEQ ID NO. 2); VVECitHQSAC (SEQ ID NO. 3); FTNCitINKLK (SEQ ID NO. 4); LRSCitIEVLK (SEQ ID NO. 5); VLKCitKVIEK (SEQ ID NO. 6); IKICitSCRGS (SEQ ID NO. 7); LPSCitDRQHL (SEQ ID NO. 8); FRHCitHPDEA (SEQ ID NO. 9); FPSCitGKSSS (SEQ ID NO. 10); IQQCitMDGSL (SEQ ID NO. 11); LTQCitGSVLR (SEQ ID NO. 12); YHFCitVGSEA (SEQ ID NO. 13); YDPCitNNSPY (SEQ ID NO. 14); VSFCitGADYS (SEQ ID NO. 15); YSLCitAVRMK (SEQ ID NO. 16); MKICitPLVTQ (SEQ ID NO. 17); YRACitPAKAA (SEQ ID NO. 18); WQKCitQKQVK (SEQ ID NO. 19); IQNCitQDGSV (SEQ ID NO. 20); WYNCitCHAAN (SEQ ID NO. 21); YSMCitKMSMK (SEQ ID NO. 22); MKICitPFFPQ (SEQ ID NO. 23); LHPCitNLILY (SEQ ID NO. 24); VATCitDNCCI (SEQ ID NO. 25); LDECitFGSYC (SEQ ID NO. 26); LKSCitIMLEE (SEQ ID NO. 27); FQKCitLDGSV (SEQ ID NO. 28); YALCitVELED (SEQ ID NO. 29); WNGCitTSTA (SEQ ID NO. 30); WKTCitWYSMK (SEQ ID NO. 31); YATCitSSAVR (SEQ ID NO. 32); VRLCitSSVPG (SEQ ID NO. 33); LNDCitFANYI (SEQ ID NO. 34); MLQCitEEAEN (SEQ ID NO. 35); LNLCitETNLD (SEQ ID NO. 36); and VETCitDGQVI (SEQ ID NO. 37), together with a pharmaceutically acceptable carrier.

According to still another aspect of the present invention is a diagnostic method for the detection of citrullinated antigen MHC class II cell complexes, said method comprising;

incubating an isolated sample of peripheral blood mononuclear cells from a subject with one or more citrullinated peptide antigens;

detecting the formation of citrullinated peptide antigen MHC class II cell complexes, such detection indicating a likelihood of evoking a T cell response leading to RA in said subject.

According to another aspect of the present invention is a method for preventing the activation of T cells by a citrullinated peptide MHC class II complex in a subject, said method comprising administering antibodies targeted to said complex.

According to another aspect of the present invention is a method for preventing the conversion of an arginine to citrulline in a potentially antigenic peptide and thus the formation of citrullinated peptide MHC class II complexes in a subject, said method comprising administering an antagonist or inhibitor of peptidylarginine deiminase to said subject.

According to yet another aspect of the present invention is a screening method to identify pharmaceutical compounds that may block the binding of a citrullinated peptide to a MHC class II molecule having the shared epitope, the method comprising;

administering to a transgenic DR4-IE tg mouse a candidate pharmaceutical compound; and measuring T cell activity and/or measuring citrullinated peptide/MHC class II molecule complex formation, wherein decreased T cell activity and/or decreased complex formation indicates said candidate pharmaceutical compound affects the binding of said citrullinated peptide to the MHC class II molecule.

According to another aspect of the present invention is a method of inducing rheumatoid arthritis in an animal to provide an animal model for the study of rheumatoid arthritis, comprising administering to said animal a rheumatoid arthritis inducing amount of a composition comprising a citrullinated peptide together with a pharmaceutically acceptable carrier. Administration may be done by injection.

According to still another aspect of the present invention is a method to make a citrullinated peptide antigen capable of binding to an MHC class II molecule with a shared epitope, said method comprising:

(a) adding peptidyl deiminase to an endogenous or exogenous solubilized protein that contains at least one arginine amino acid residue for a time sufficient to convert the arginine to citrulline; and (b) isolating the protein from (a).

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

BRIEF DESCRIPTION OF THE DRAWINGS

The present invention will become more fully understood from the detailed description given herein and from the accompanying drawings, which are given by way of illustration only and do not limit the intended scope of the invention.

In FIG. 1B HLA-DR restriction of the recall T cell response was determined by incubating draining lymph node cells in vitro without antigen (control), with 10 µg/ml of the immunizing antigen (P4D left panel, P4Cit right panel), or in the presence of immunizing antigen (10 µg/ml) and anti-DR antibody (DR). Results represent the average proliferative response±SD of 4 mice for each immunizing antigen. FIG. 1C shows the IFN-γ production in response to in vitro challenge with 10 µg/ml of the immunizing peptide (P4D, P4Cit, or P4R). Cytokine production was determined by ELISA and represents the average antigen specific IFN-γ production±SD of 4 mice for each peptide tested.

In FIG. 2A DR4-IE tg mice were immunized with the indicated peptides and 10 days later draining lymph node cells were challenged in vitro with the same peptide at various concentrations. Data represents the average proliferative response±SEM of 8 mice for each peptide tested. FIG. 2B shows the specificity and HLA-DR restriction of the T cell recall response from Vim R70Cit immunized mice (left panel) and Vim 65-77 immunized mice (right panel). Draining lymph node cells were challenged with the immunizing peptide, the immunizing peptide plus anti-DR antibody (DR), the unmodified vimentin peptide (65-77 in left panel), or the citrulline containing vimentin peptide (R70Cit in right panel). The concentration used for in vitro challenge was 10 µg/ml and the results represent the average stimulation index±SEM of 4 mice for each immunizing antigen. FIG. 2C shows IFN-γ production in response to an in vitro challenge with varying concentrations of the immunizing peptide (Vim R70Cit or Vim 65-77). Cytokine production was determined by ELISA and represents the average antigen specific IFN-γ production±SD of 4 mice for each peptide tested.

DETAILED DESCRIPTION OF THE PREFERRED EMBODIMENTS

Figure 1A:
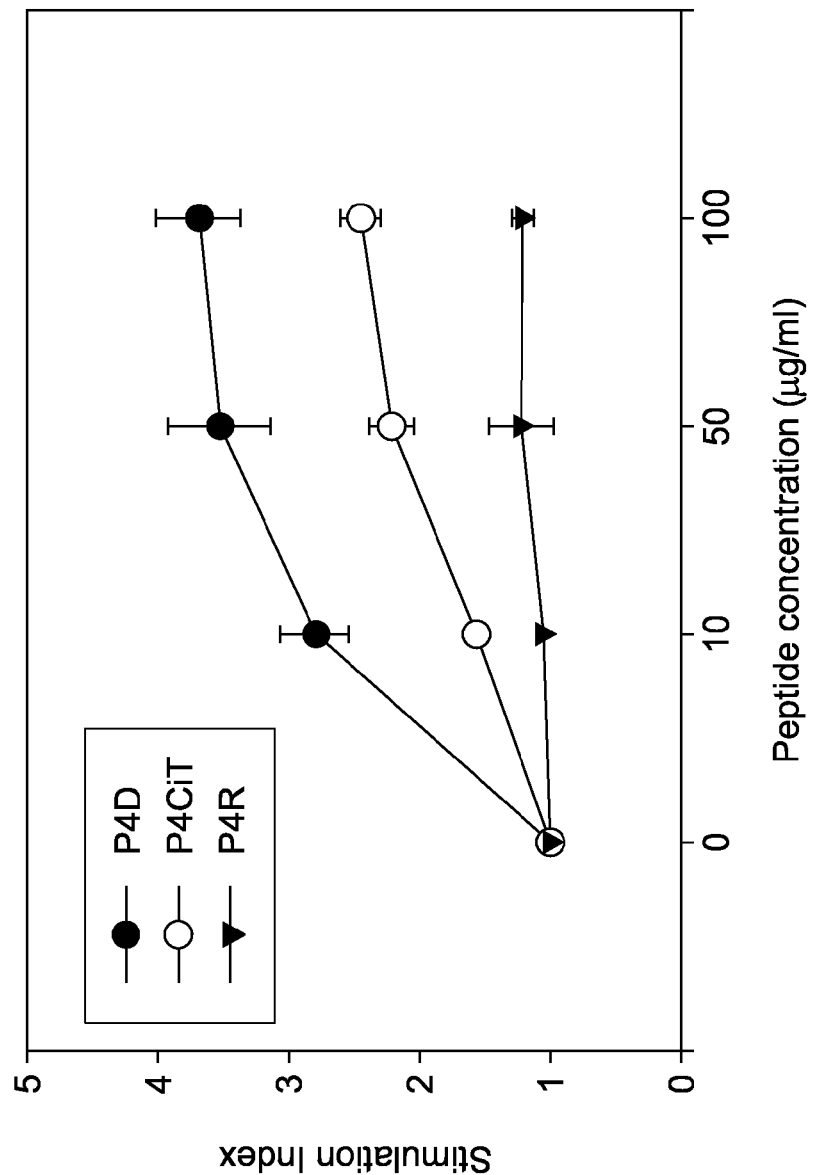
FIGS. 1A, 1B and 1C are graphs representing an analysis of the T cell immune response in DR4-IE tg mice to peptides containing arginine (P4R), citrulline (P4Cit), or aspartic acid (P4D) at the position that interacts with the P4 pocket formed by the shared epitope. In graph 1A DR4-IE tg mice were immunized with the indicated peptides and 10 days later draining lymph node cells were challenged in vitro with the same peptide at various concentrations. Data represents the average proliferative response±SEM of 8 mice for each peptide tested.

The Applicant has developed and identified novel citrullinated antigenic peptides that specifically bind to MHC class II molecules with the shared epitope leading to the activation of T cells and consequently, the development of Rheumatoid Arthritis. The conversion of arginine to citrulline at a peptide side-chain position that interacts with the shared epitope (P4) significantly increases peptide-MHC affinity and leads to the activation of CD4+ T cells. Such T cell activation further leads to synovial inflammation and the development of Rheumatoid Arthritis. It is understood by those of skill in the art that the citrullinated peptide antigens of the invention may be involved in a variety of autoimmune disorders characterized by the binding and formation of a citrullinated peptide/MHC class II complex resulting in the activation of T cells and a development of an inflammatory response. Therefore, the present invention has several applications for autoimmune disorders involving such an etiology.

Using HLA-DRB1*0401 transgenic (DR4-IE tg) mice, the Applicant has demonstrated increased T cell responses to citrulline containing peptides. Using a model to predict MHC-peptide affinity, candidate T cell epitopes were developed and selected for study, including those from vimentin, fibrinogen and proteoglycan aggrecan. In the case of proteoglycan aggrecan, this protein normally contains a negatively charged aspartic acid (D) that interacts with the P4 shared epitope. Fibrinogen and vimentin peptides were chosen based on the property of binding to DRB1*0401 in a register that would position either arginine or citrulline at the positively charged P4 anchoring pocket (shared epitope). The conversion of arginine to citrulline, a process which replaces the charged imino side-chain group with an uncharged carbonyl, dramatically increased the affinity of the peptide for DRB1*0401. Furthermore, this post-translational modification was necessary to elicit a CD4+ T cell response to these peptides in DR4-IE tg mice. Peptide affinity for a number of HLA alleles was assessed and showed that only MHC class II molecules with the shared epitope had an increased affinity for the citrulline containing peptide. These studies, which identify a novel peptide-MHC interaction, help to explain the molecular basis of disease associated HLA alleles in RA and now provide for new diagnostic and therapeutic strategies for Rheumatoid Arthritis. The third hyper-variable region of MHC class II molecules associated with RA contains the amino acid sequence Q/R, K/R, R, A, A, spanning positions 70-74 of the DRβ chain. This shared epitope region forms one of the major peptide anchoring pockets known as P4, and is positively charged due to the K or R at position 71 which can make direct contact with side chain residues from the antigenic peptide (Dessen A, Lawrence C M, Cupo S, Zaller D M, Wiley D C. 1997. X-ray crystal structure of HLA-DR4 (DRA*0101, DRB1*0401) complexed with a peptide from human collagen II. *Immunity.* 7:473; Stern L J, Brown J H, Jardetzky T S, Gorga J C, Urban R G, Strominger J L, Wiley D C. 1994. Crystal structure of the human class II MHC protein HLA-DR1 complexed with an influenza virus peptide. *Nature.* 368:215). Previous studies on peptide-MHC affinity have shown that K or R at position 71 dictates the properties of the amino acid that can interact at this P4 pocket (Hammer J., Gallazzi F., Bono E., Karr R. W., Guenot J., Valsasnini P., Nagy Z. A., Sinigaglia F. 1995. Peptide binding specificity of HLA-DR4 molecules: correlation with rheumatoid arthritis association. *J. Exp. Med.* 181:1847). In general, MHC with the shared epitope have a high affinity for negatively charged or uncharged polar amino acids, while positively charged amino acids (i.e. arginine) inhibit peptide binding (Hammer J, Bono E, Gallazzi F, Belunis C, Nagy Z, Sinigaglia F. 1994. Precise prediction of major histocompatibility complex class I-peptide interaction based on peptide side chain scanning. *J. Exp. Med.* 180:2353; Hammer J., Gallazzi F., Bono E., Karr R. W., Guenot J., Valsasnini P., Nagy Z. A., Sinigaglia F. 1995. Peptide binding specificity of HLA-DR4 molecules: correlation with rheumatoid arthritis association. *J. Exp. Med.* 181:1847). The Applicant has demonstrated that deimination converting positively charged arginine to polar but uncharged citrulline (a post-translational modification) increases the affinity to the shared epitope P4 pocket. Since amino acid interactions at MHC anchoring pockets are not only dependent on the charge of the residue but also the size, the Applicant also confirmed that the P4 pocket formed by the shared epitope was large enough to accommodate the side chain of citrulline. This was verified by molecular modeling using the crystal structure of DRB1*0401 and DRB1*0101 (data not shown). Based on the charge properties of the P4 shared epitope and the size of this pocket, peptide bound citrulline was predicted to interact favourably at the P4 anchoring pocket of HLA*0401 and HLA*0101.

Figure 1B:
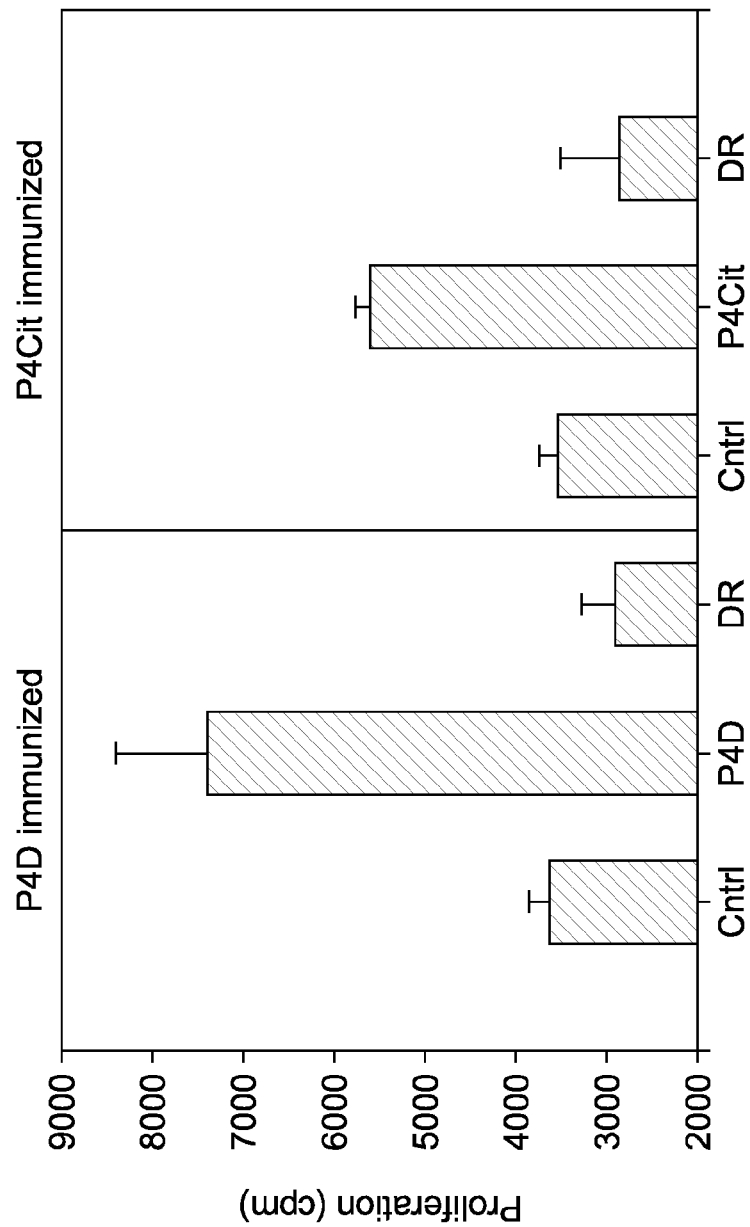
Figure 1C:
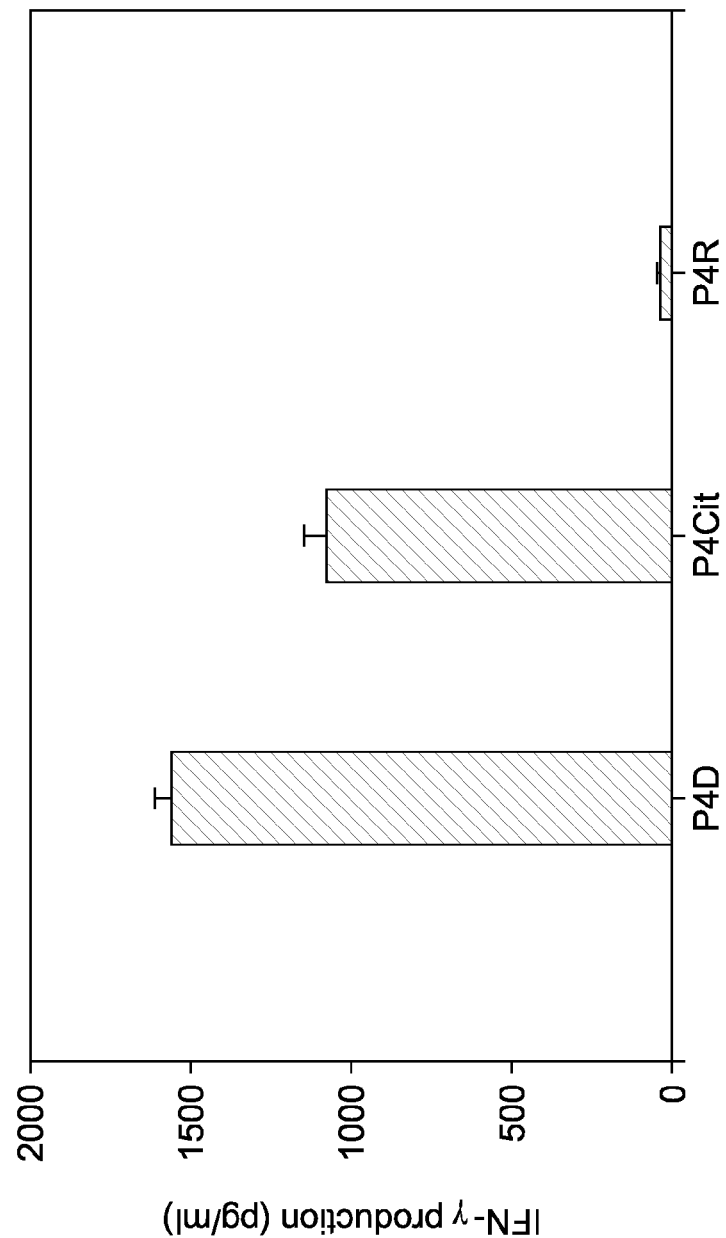
Figure 2A:
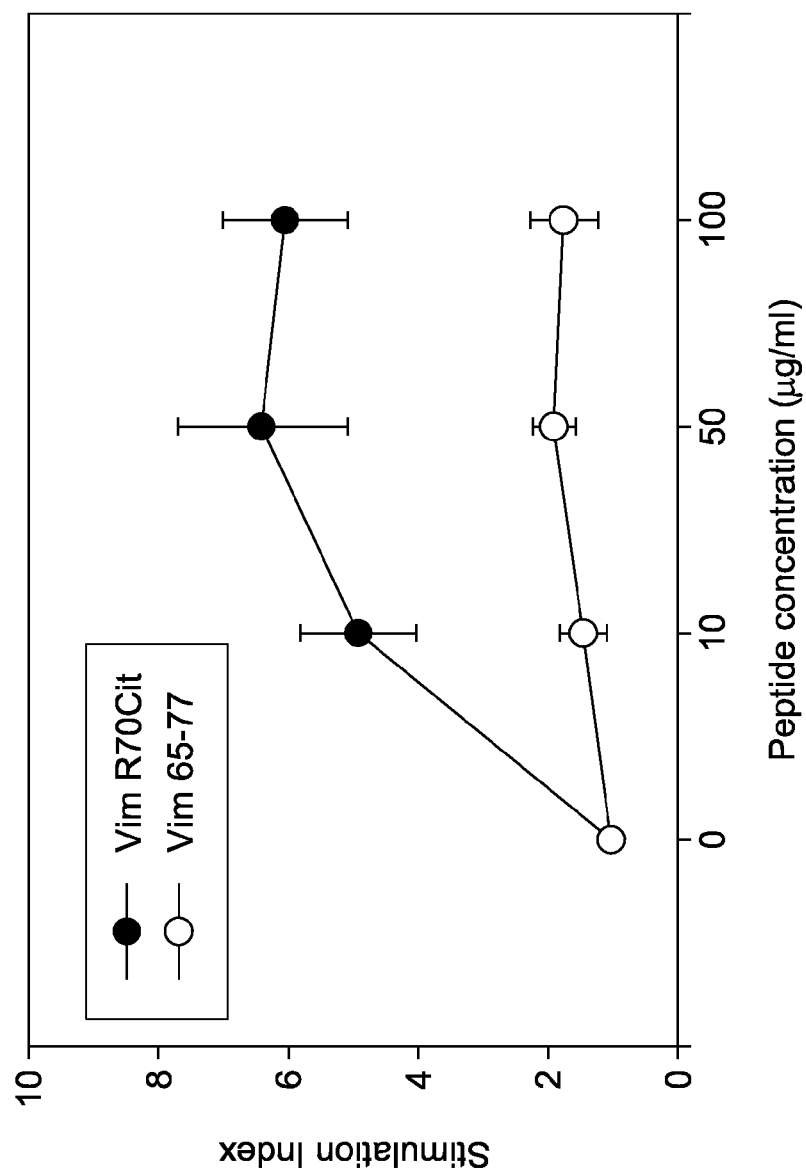
FIGS. 2A, 2B and 2C are graphs showing an analysis of the T cell immune response in DR4-IE tg mice to the unmodified vimentin peptide (Vim 65-77) or the citrulline containing vimentin peptide (Vim R70Cit).
Figure 2B:
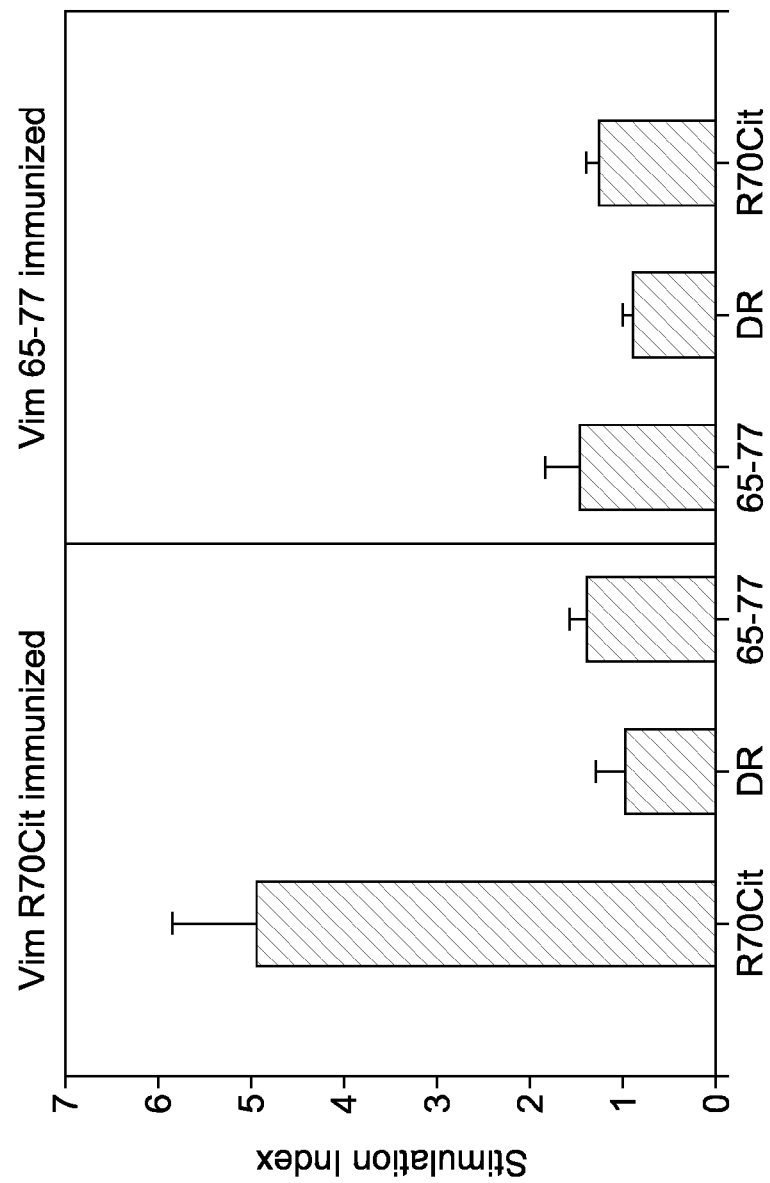
Figure 2C:
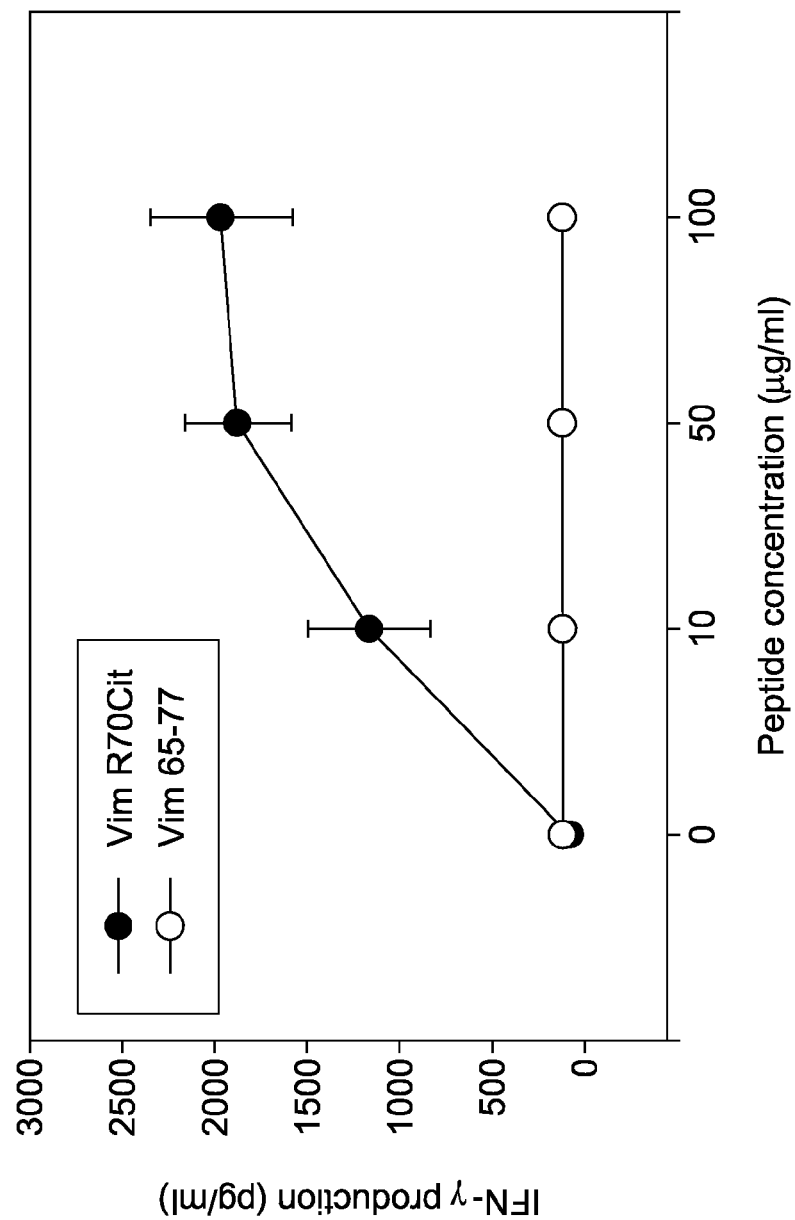
Figure 3:
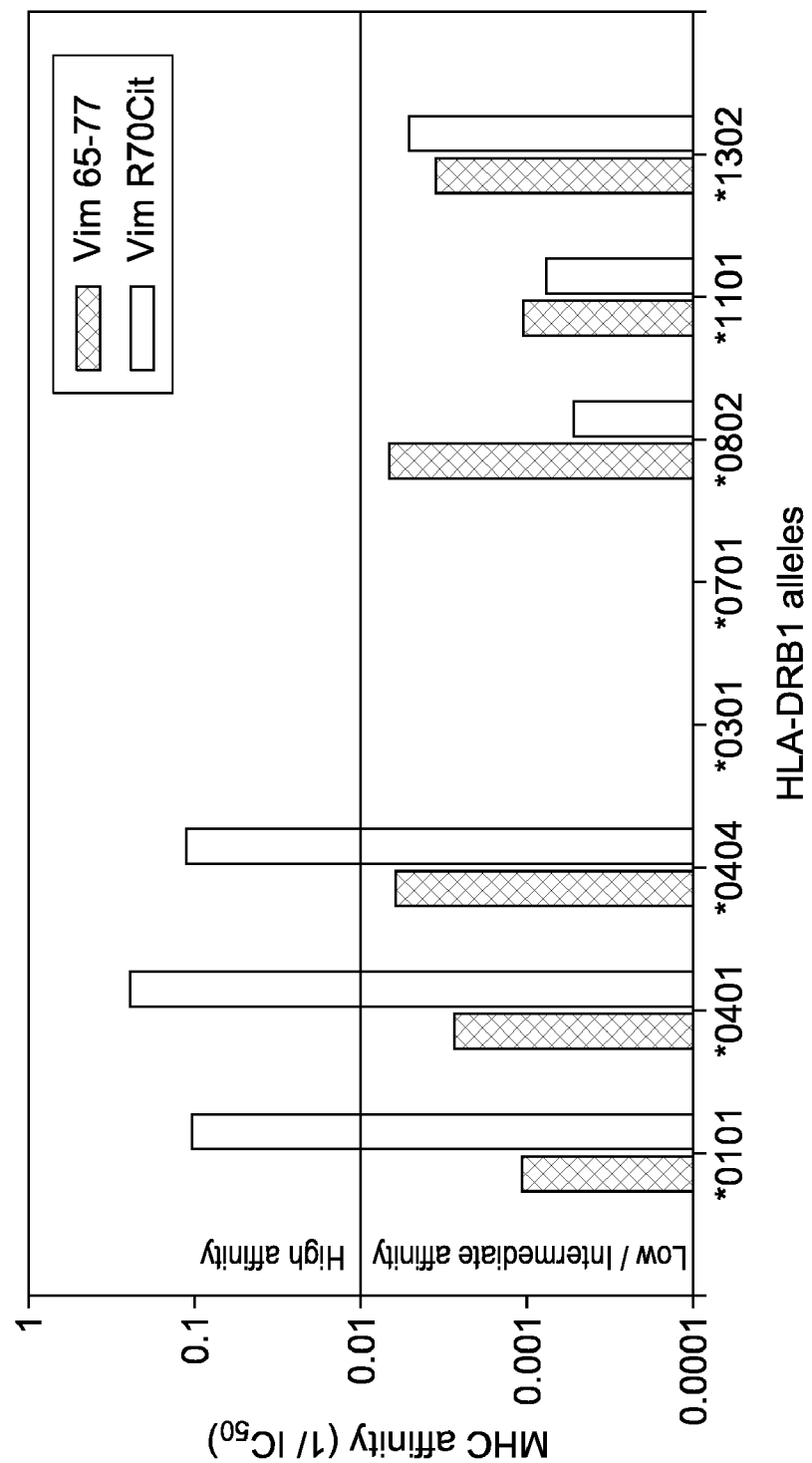
FIG. 3 is a graph showing the relative affinities of Vim 65-77 and Vim R70Cit for purified MHC class II molecules. Binding affinities to shared epitope positive (*0101, 0401, *0404) and negative alleles (*0301, *0701, *0802, *1101, *1302) were determined as described in the Examples described herein. Peptides with $IC_{50}$ values less than 100 nM are considered to be high affinity binders.

A peptide sequence was developed and chosen that was demonstrated by the Applicant to activate CD4+ T cells from DR4-IE tg mice. This peptide (from the cartilage proteoglycan aggrecan) normally contains a negatively charged aspartic acid (D) that interacts with the P4 shared epitope (P4D). Two additional peptides were synthesized based on this sequence: one had aspartic acid substituted by arginine (P4R); and the other had citrulline substituted at this position (P4Cit). DR4-IE tg mice were then immunized with these peptides and T cell responses were assessed 10 days later. The peptide P4D induced a strong proliferative response that was accompanied by IFN-γ production (FIGS. 1A and 1B). The peptide containing the arginine substitution (P4R), however, did not induce T cell proliferation or cytokine production in these mice. In contrast to an absent response for P4R, P4Cit induced T cell proliferation and IFN-γ production. To confirm that P4Cit was activating T cells through peptide-MHC presentation, anti-DR antibody was used to inhibit TCR interaction with the peptide-MHC complex (FIG. 1B). This treatment inhibited the proliferative response to P4Cit and P4D. Potential T cell epitopes from a protein target of anti-citrulline antibodies in RA patients were identified. Vimentin was selected since autoantibodies to this protein are frequently found in patients expressing the shared epitope (Goldbach-Mansky R, Lee J, McCoy A, Hoxworth J, Yarboro C, Smolen J S, Steiner G, Rosen A, Zhang C, Menard H A, Zhou Z J, Palosuo T, Van Venrooij W J, Wilder R L, Klippel J H, Schumacher H R Jr, El-Gabalawy H S. 2000. Rheumatoid arthritis associated autoantibodies in patients with synovitis of recent onset. *Arthritis Res.* 2:236). A candidate T cell epitope from human vimentin was identified using a predictive model for peptide-MHC affinity (Hammer J, Bono E, Gallazzi F, Belunis C, Nagy Z, Sinigaglia F. 1994. Precise prediction of major histocompatibility complex class II-peptide interaction based on peptide side chain scanning. *J. Exp. Med.* 180:2353). This peptide was selected based on the properties of having favourable interactions with the MHC anchoring pockets P1, P6, and P9, and having an arginine at the P4 shared epitope. Two peptides were synthesized, one containing the unmodified peptide Vimentin 65-77 and the other Vimentin R70Cit, in which arginine was substituted by citrulline. T cell responses to these peptides were then characterized using DR4-IE tg mice. As expected, the unmodified peptide Vim 65-77 did not induce T cell activation, however, Vim R70Cit stimulated a strong proliferative response that was accompanied by IFN-γ production (FIGS. 2A and 2C). T cell responses to Vim R70Cit could also be inhibited using anti-DR antibodies, confirming the MHC class II restricted immune response (FIG. 2B). It was also demonstrated that T cells primed by Vim R70Cit could not be activated by the unmodified peptide, further supporting that Vim 65-77 does not interact productively with the DR4 binding groove (FIG. 2B).

To confirm that the conversion of arginine to citrulline could increase peptide affinity for MHC class II molecules that contained the shared epitope, peptide competition assays were conducted to determine the relative affinity of Vim 65-77 and Vim R70Cit for purified MHC that were either shared epitope positive (DRB1*0101, *0401, *0404) or shared epitope negative (DRB1*0301, *0701, *0802, *1101, *1302). While Vim 65-77 had a low to intermediate affinity for all MHC tested, Vim R70Cit bound *0101, *0401, and *0404 with a strikingly high affinity. Compared to the unmodified peptide, the citrulline containing peptide bound with 100 fold, 90 fold, and 20 fold higher affinity to *0101, *0401, and *0404 respectively. Most importantly, the conversion of arginine to citrulline did not increase peptide affinity for any shared epitope negative MHC tested.

The Applicant's results indicated that the differential binding properties of DRB1 alleles to either arginine or citrulline at P4 explain how MHC class II molecules are disease associated, non-associated, or protective. First, the conversion of peptide bound arginine to citrulline causes a 100-fold increase in affinity for MHC with the shared epitope. This could result in a higher density of peptide-MHC complexes on antigen presenting cells which may exceed the "biochemical margin of safety" necessary for T cell activation (Peterson D A, DiPaolo R J, Kanagawa O, Unanue E R. 1999. Cutting edge: negative selection of immature thymocytes by a few peptide-MHC complexes: differential sensitivity of immature and mature T cells. *J. Immunol.* 162:3117; DiPaolo R J, Unanue E R. 2001. The level of peptide-MHC complex determines the susceptibility to autoimmune diabetes: studies in HEL transgenic mice. *Eur. J. Immunol.* 31:3453; Yagi J, Janeway C A Jr. 1990. Ligand thresholds at different stages of T cell development. *Int. Immunol.* 2:83). Second, non-associated MHC class II molecules (e.g. *0301) may contain P4 pockets that lack the proper size or charge to productively accommodate the large polar side-chains of arginine or citrulline, and would therefore be unable to bind and present peptides regardless of the state of modification (Ghosh P, Amaya M, Mellins E, Wiley D C. 1995. The structure of an intermediate in class II MHC maturation: CLIP bound to HLA-DR3. *Nature.* 378:457). Finally, disease protective MHC may interact productively with both arginine and citrulline at P4 resulting in peptide-MHC ligands that may induce negative selection, lead to the production of CD4$^+$ CD25$^+$ regulatory T cells (Jordan M S, Boesteanu A, Reed A J, Petrone A L, Holenbeck A E, Lerman M A, Naji A, Caton A J. 2001. Thymic selection of CD4+CD25+ regulatory T cells induced by an agonist self-peptide. *Nat. Immunol.* 2:301), or simply remain within the "biochemical margin of safety" (Peterson D A, DiPaolo R J, Kanagawa O, Unanue E R. 1999. Cutting edge: negative selection of immature thymocytes by a few peptide-MHC complexes: differential sensitivity of immature and mature T cells. *J. Immunol.* 162: 3117).

The present invention demonstrates a set of peptides based on fibrinogen and vimentin amino acid sequences. The term "peptide" as used herein is defined as a chain of amino acid residues, usually having a defined sequence. As used herein the term peptide is mutually inclusive of the terms "peptides" and "proteins". In a preferred aspect, the fibrinogen and vimentin sequences are human amino acid sequences. The invention also encompasses both the full length fibrinogen and vimentin amino acid sequences having at least one of the arginine amino acids converted to a citrulline, or fragments thereof. The limitation being that any fragment of any desired length has at least one citrulline that binds with high affinity to any MHC class II molecule with the shared epitope. One of skill in the art would understand that several additional sequences within vimentin and the alpha and beta chains of fibrinogen are predicted to bind the HLA*0401 allele in a register that would position arginine or citrulline at P4 and thus are embodied in the present invention. Furthermore, the invention encompasses any peptide that is demonstrated to be a potential target of anti-citrulline antibodies in RA patients. This suggests that a number of unique pathogenic peptides give rise to activated T cell with a heterogeneous array of specificities. In one aspect any endogenous or exogenous protein or peptide that is susceptible to modification by peptidylarginase deiminase, and further has the property of binding MHC Class II molecules with the shared epitope, is embodied by the present invention. Such proteins and peptides in one aspect can be found present in the joints and may include, but are not limited to, vimentin and fibrinogen.

The citrullinated peptides of the invention bind with high affinity to a MHC class II molecule having the shared epitope. It is understood by one of skill in the art, that "high affinity" as used herein refers to the capability of the citrullinated peptides to bind with higher or increased affinity to the MHC class II molecule having the shared epitope compared with a non-citrullinated peptide, such as a peptide having an arginine amino acid rather than citrulline. It is further understood that such binding affinity can be readily established for example in vitro using a peptide binding assay in which a sample peptide is used to displace a standard peptide (see example section).

In one embodiment, proteins of the present invention may include but are not limited to citrullinated peptides comprising at least one of the amino acid sequences selected from the group consisting of: SAVRACitSSVPGVR (SEQ ID NO. 1); FSMCitIVCLV (SEQ ID NO. 2); VVECitHQSAC (SEQ ID NO. 3); FTNCitINKLK (SEQ ID NO. 4); LRSCitIEVLK (SEQ ID NO. 5); VLKCitKVIEK (SEQ ID NO. 6); IKICitSCRGS (SEQ ID NO. 7); LPSCitDRQHL (SEQ ID NO. 8); FRHCitHPDEA (SEQ ID NO. 9); FPSCitGKSSS (SEQ ID NO. 10); IQQCitMDGSL (SEQ ID NO. 11); LTQCitGSVLR (SEQ ID NO. 12); YHFCitVGSEA (SEQ ID NO. 13); YDPCitNNSPY (SEQ ID NO. 14); VSFCitGADYS (SEQ ID NO. 15); YSLCitAVRMK (SEQ ID NO. 16); MKICitPLVTQ (SEQ ID NO. 17); YRACitPAKAA (SEQ ID NO. 18); WQKCitQKQVK (SEQ ID NO. 19); IQNCitQDGSV (SEQ ID NO. 20); WYNCitCHAAN (SEQ ID NO. 21); YSMCitKMSMK (SEQ ID NO. 22); MKICitPFFPQ (SEQ ID NO. 23); LHPCitNLILY (SEQ ID NO. 24); VATCitDNCCI (SEQ ID NO. 25); LDECitFGSYC (SEQ ID NO. 26); LKSCitIMLEE (SEQ ID NO. 27); FQKCitLDGSV (SEQ ID NO. 28); YALCitVELED (SEQ ID NO. 29); WNGCitTSTA (SEQ ID NO. 30); WKTCitWYSMK (SEQ ID NO. 31); YATCitSSAVR (SEQ ID NO. 32); VRLCitSSVPG (SEQ ID NO. 33); LNDCitFANYI (SEQ ID NO. 34); MLQCitEEAEN (SEQ ID NO. 35); LNLCitETNLD (SEQ ID NO. 36); and VETCitDGQVI (SEQ ID NO. 37).

Certain of these peptide sequences may contain additional arginines that may be converted to citruline via the action of the enzyme peptidylarginine deiminase. The peptides of the invention may be of about at least 9 amino acids in length and about 9 to about 55 amino acids in length and include any ranges of length therein (i.e. 9-50, 9-45, 9-40, 9-35, 9-30, 9-25, 9-20, 9-15, etc.) as is understood by one of skill in the art. Peptides of over about 55 amino acids in length are also encompassed by the present invention. The length of peptide being only restricted by its binding capability to a MHC Class II molecule having the shared epitope. The peptides of the invention may also include dimers and trimers of the peptides as well as additional stabilizing flanking sequences as is understood by those of skill in the art and described for example in U.S. Pat. No. 5,824,315 and U.S. Pat. No. 6,184, 204 (the disclosures of which are incorporated herein by reference in their entirety). A multimer according to the invention can either be a homomer, consisting of a multitude of the same peptide, or a heteromer consisting of different peptides. As stated, the amino acid sequences of the peptides according to the invention can be flanked by random amino acid sequences. Preferred are flanking sequences that have a stabilizing effect on the peptides, thus increasing their biological availability. In addition, other peptidomimetics are also useful in the peptides of the present invention. For a general review see A. F. Spatola, in Chemistry and Biochemistry of Amino Acids, Peptides and Proteins, B. Weinstein, eds., Marcel Dekker, New York, p. 267 (1983). The peptides of the invention also encompass peptides that have been modified by, for example, phosphorylation, glycosylation or lipidation. Furthermore, the polypeptides of the present invention may also encompass "functionally equivalent variants" or "analogues" of the peptides. As such, this would include but not be limited to peptides and polypeptides with partial sequence homology, peptides having one or more specific conservative and/or non-conservative amino acid changes and peptide conjugates which do not alter the biological or structural properties of the peptide (i.e. the ability to bind to an MHC class II molecule having the shared epitope).

In terms of "functional analogues", it is well understood by those skilled in the art, that inherent in the definition of a biologically functional peptide analogue is the concept that there is a limit to the number of changes that may be made within a defined portion of the molecule and still result in a molecule with an acceptable level of equivalent biological activity, which, in this case, would include the ability to bind to an MHC class II molecule having a shared epitope. A plurality of distinct peptides/proteins with different substitutions may easily be made and used in accordance with the invention. It is also understood that certain residues are particularly important to the biological or structural properties of a protein or peptide such as residues in the receptor recognition region, such residues of which may not generally be exchanged.

Functional analogues can be generated by conservative or non-conservative amino acid substitutions. Amino acid substitutions are generally based on the relative similarity of the amino acid side-chain substituents, for example, their hydrophobicity, hydrophilicity, charge, size and the like. Thus, within the scope of the invention, conservative amino acid changes means, an amino acid change at a particular position which is of the same type as originally present; i.e. a hydrophobic amino acid exchanged for a hydrophobic amino acid, a basic amino acid for a basic amino acid, etc. Examples of conservative substitutions include the substitution of nonpolar (hydrophobic) residues such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another, the substitution of a branched chain amino acid, such as isoleucine, leucine, or valine for another, the substitution of one aromatic amino acid, such as phenylalanine, tyrosine or tryptophan for another. Such amino acid changes result in functional analogues in that they do not significantly alter the overall charge and/or configuration of the peptide. Examples of such conservative changes are well-known to the skilled artisan and are within the scope of the present invention. Conservative substitution also includes the use of a chemically derivatized residue in place of a non-derivatized residue provided that the resulting peptide is a biologically functional equivalent to the peptides of the invention. Therefore, the citrullinated peptides of the present invention encompass a peptide having an amino acid sequence that differs from SEQ ID Nos. 1-37 by one or more conservative amino acid substitutions. The citrullinated peptides of the invention also encompass a peptide having an amino acid sequence that differs from SEQ ID Nos. 1-37 by a single mutation, where the single mutation represents a single amino acid deletion, insertion or substitution.

The peptides of the present invention may be made by methods known to those of skill in the art most notably and preferably by chemical synthesis using techniques well known in the chemistry of proteins such as solid phase synthesis (Merrifield (1964) J. Am. Chem. Assoc. 65:2149; J. Amer. Chem. Soc. 85:2149 (1963); and Int. J. Peptide Protein Res. 35:161-214 (1990)) or synthesis in homogenous solution (Methods of Organic Chemistry, E. Wansch (Ed.) Vol. 15, pts. I and II, Thieme, Stuttgart (1987) to generate synthetic peptides. Citrulline is a post-translationally modified arginine that is created through the process of deimination which is catalyzed by the enzyme peptidylarginine deiminase (PAD) that removes a positive charge from arginine and makes the resulting citrulline polar in nature.

In one embodiment, citrullinated peptides of the invention can be made from known commercially available sources of vimentin and fibrinogen. In this aspect, lyophilized vimentin or fibrinogen are reconstituted in an appropriate buffer to which the enzyme peptidylarginine deiminase is added. The solution is allowed to stand at an appropriate temperature for a time sufficient to cause modification of arginine residues to citrulline and thus create a citrullinated vimentin or fibrinogen protein. The citrullinated protein is then isolated by the removal of the enzyme using a high molecular weight membrane to separate the enzyme or other methods of chromatography. One of skill in the art will understand that the temperature of incubation, buffer condition and time of incubation may vary depending on the protein that is being deiminated (Christine Masson-Bessiere et al., 2001. The Major Synovial Targets of the Rheumatoid Arthritis-Specific Antifilaggrin Autoantibodies Are Deiminated Forms of the ⊢and ⥉Chains of Fibrin 1 *The Journal of Immunology* 166: 4177-4184). In one aspect of the present invention, citrullinated fibrinogen was made by obtaining plasminogen-depleted human fibrinogen (Calbiochem, San Diego, Calif.) and incubating this protein at 0.86 mg/ml with rabbit skeletal muscle PAD (7 U/mg fibrinogen; Sigma) in 0.1 M Tris-HCl (pH 7.4), 10 mM $CaCl_2$, and 5 mM DTT for 2 hours at 50° C. for deimination of the protein.

The citrullinated proteins may be further isolated and purified by methods selected on the basis of properties revealed by its sequence. Purification can be achieved by protein purification procedures such as chromatography methods (gel-filtration, ion-exchange and immunoaffinity), by high-performance liquid chromatography (HPLC, RP-HPLC, ion-exchange HPLC, size-exclusion HPLC, high-performance chromatofocusing and hydrophobic interaction chromatography) or by precipitation (immunoprecipitation). Polyacrylamide gel electrophoresis can also be used to isolate the citrullinated proteins based on the molecular weight of the protein, charge properties and hydrophobicity. The purified citrullinated proteins can be used in further biochemical analyses to establish secondary and tertiary structure which may aid in the design of pharmaceuticals to interact with the protein, alter the protein charge configuration or charge interaction with other proteins or alter its function.

Alternatively, the citrullinated peptides of the invention may be made by the use of recombinant DNA techniques known to one skilled in the art. As citrulline is not encoded by any trinucleotide sequence, a nucleic acid sequence encoding for arginine may be used with the resultant protein sequence being modified using peptidylarginine deiminase (PAD) to convert the arginine to citrulline. It is further within the scope of the invention to use a nucleic acid sequence encoding for glutamine, an amino acid that resembles citrulline. In this manner, a naturally occurring sequence that contains arginine can be used in which the arginine is substituted with glutamine in order to resemble citrulline. Nucleic acid sequences which encode for the selected peptides of the invention may be incorporated in a known manner into appropriate expression vectors (i.e. recombinant expression vectors). Possible expression vectors include (but are not limited to) cosmids, plasmids, or modified viruses (e.g. replication defective retroviruses, adenoviruses and adeno-associated viruses, lentiviruses, herpes viruses, poxviruses), so long as the vector is compatible with the host cell used. The expression "vector is compatible with the host cell" is defined as contemplating that the expression vector(s) contain a nucleic acid molecule of the invention (hereinafter described) and attendant regulatory sequence(s) selected on the basis of the host cell(s) to be used for expression, said regulatory sequence(s) being operatively linked to the nucleic acid molecule. "Operatively linked" is intended to mean that the nucleic acid is linked to regulatory sequence(s) in a manner which allows expression of the nucleic acid. Suitable regulatory sequences may be derived from a variety of sources, including bacteria), fungal, or viral genes. (For example, see the regulatory sequences described in Goeddel, Gene Expression Technology Methods in Enzymology 185, Academic Press, San Diego, Calif. (1990). Selection of appropriate regulatory sequence(s) is dependent on the host cell(s) chosen, and may be readily accomplished by one of ordinary skill in the art. Examples of such regulatory sequences include the following: a transcriptional promoter and enhancer, RNA polymerase binding sequence, or a ribosomal binding sequence (including a translation initiation signal). Depending on the host cell chosen and the expression vector employed, other additional sequences (such as an origin of replication, additional DNA restriction sites, enhancers, and sequences conferring inducibility of transcription) may be incorporated into the expression vector.

The peptides of the invention may also be produced recombinantly in association with a soluble MHC molecule using a variety of methods known to those of skill in the art (i.e. Hugues, S et al (2002) Generation and use of alternative multimers of peptide/MHC complexes. Journal of Immunological Methods. 268:83-91 (the disclosure of which is incorporated herein in its entirety). Methods for making peptide/MHC class II soluble complexes are also provided in U.S. Pat. No. 5,869,279 (the disclosure of which is incorporated herein in its entirety).

It is further contemplated that the invention encompasses vectors which comprise nucleic acids coding for at least one member from the group consisting of cytokines, lymphokines and immunomodulatory molecules. Said nucleic acid sequences can be contiguous with sequences coding for the citrullinated peptide antigens of the invention, or encoded on distinct nucleic acids.

An embodiment of the present invention further encompasses pharmaceutical compositions comprising one or more citrullinated peptides for administration to subjects in a biologically compatible form suitable for administration in vivo. The citrullinated peptides for use within a pharmaceutical composition may be made chemically or by recombinant DNA techniques. The administration of the citrullinated peptide antigens of the invention may act to desensitize the immune system in those patients having auto-responsive T cells and thus reduce the inflammatory response over time. The peptides of the invention may be provided within DNA expression vectors as described above that are formulated in a suitable pharmaceutical composition.

By "biologically compatible form suitable for administration in vivo" is meant a form of the substance to be administered in which any toxic effects are outweighed by the therapeutic effects. Administration of a therapeutically active amount of the pharmaceutical compositions of the present invention, or an "effective amount", is defined as an amount effective at dosages and for periods of time, necessary to achieve the desired result of eliciting an immune response in a human. A therapeutically effective amount of a substance may vary according to factors such as the disease state/health, age, sex, and weight of the recipient, and the inherent ability of the particular polypeptide, nucleic acid coding therefor, or recombinant virus to elicit a desired immune response. Dosage regima may be adjusted to provide the optimum therapeutic response. For example, several divided doses may be administered daily or on at periodic intervals, and/or the dose may be proportionally reduced as indicated by the exigencies of the therapeutic situation. The amount of citrullinated peptide antigen for administration will depend on the route of administration, time of administration and varied in accordance with individual subject responses. Suitable administration routes are intramuscular injections, subcutaneous injections, intravenous injections or intraperitoneal injections, oral and intranasal administration. Oral and intranasal administration are preferred administration routes.

The compositions described herein can be prepared by per se known methods for the preparation of pharmaceutically acceptable compositions which can be administered to subjects, such that an effective quantity of the active substance (i.e. citrullinated peptide) is combined in a mixture with a pharmaceutically acceptable vehicle. Suitable vehicles are described, for example, in "Handbook of Pharmaceutical Additives" (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456.

Pharmaceutical acceptable carriers are well known to those skilled in the art and include, for example, sterile saline, lactose, sucrose, calcium phosphate, gelatin, dextrin, agar, pectin, peanut oil, olive oil, sesame oil and water. Other carriers may be, for example MHC class II molecules. Soluble MHC class II molecules including monomers, dimers, trimers, tetramers, etc, as well as citrulline peptide/MHC class II complexes can be made by methods disclosed in U.S. Pat. No. 5,869,270 (the disclosure of which is incorporated herein by reference).

Furthermore the pharmaceutical composition according to the invention may comprise one or more stabilizers such as, for example, carbohydrates including sorbitol, mannitol, starch, sucrose, dextrin and glucose, proteins such as albumin or casein, and buffers like alkaline phosphates.

The pharmaceutical composition of the invention may also comprise one or more adjuvants. As is well known to those of ordinary skill in the art, the ability of an immunogen to induce/elicit an immune response can be improved if, regardless of administration formulation (i.e. recombinant virus, nucleic acid, peptide), the immunogen is coadministered with an adjuvant. Adjuvants are described and discussed in "Vaccine Design-the Subunit and Adjuvant Approach" (edited by Powell and Newman, 'Plenum Press, New York, U.S.A., pp. 61-79 and 141-228 (1995)). Adjuvants typically enhance the immunogenicity of an immunogen but are not necessarily immunogenic in and of themselves. Adjuvants may act by retaining the immunogen locally near the site of administration to produce a depot effect facilitating a slow, sustained release of immunizing agent to cells of the immune system. Adjuvants can also attract cells of the immune system to an immunogen depot and stimulate such cells to elicit immune responses. As such, embodiments of this invention encompass compositions further comprising adjuvants.

Desirable characteristics of ideal adjuvants include:
1) lack of toxicity:
2) ability to stimulate a long-lasting immune response;
3) simplicity of manufacture and stability in long-term storage;
4) ability to elicit both cellular and humoral responses to antigens administered by various routes, if required:
5) synergy with other adjuvants;
6) capability of selectively interacting with populations of antigen presenting cells (APC);
7) ability to specifically elicit appropriate Tr, TR1 or TH2 cell-specific immune responses; and
8) ability to selectively increase appropriate antibody isotype levels (for example, IgA) against antigens/immunogens.

Suitable adjuvants include, amongst others, aluminium hydroxide, aluminium phosphate, amphigen, tocophenols, monophosphenyl lipid A, muramyl dipeptide and saponins such as Quill A. Preferably, the adjuvants to be used in the tolerance therapy according to the invention are mucosal adjuvants such as the cholera toxine B-subunit or carbomers, which bind to the mucosal epithelium. The amount of adjuvant depending on the nature of the adjuvant itself as is understood by one of skill in the art.

It is further embodied within the present invention that the citrullinated peptides can be administered to a patient in combination with short double stranded RNA (less than 30 nucleotides in length) that mediate an RNA interference response against a desired gene. These target genes may be selected from one or more members of the group consisting of transcription factors, enzymes, cytokines, lymphokines and immunomodulatory molecules.

The peptides and compositions of the invention can be administered in the context of an MHC molecule. Thus, the polypeptides of this invention can be pulsed into antigen presenting cells which include, but are not limited to dendritic cells (DCs). More specifically, the citrullinated peptides may be administered to a patient via antigen pulsed dendritic cells (antigen presenting cells). In certain embodiments of the present invention use dendritic cells or progenitors thereof as antigen-presenting cells. These dendritic cells can be grown from the PBMCs (peripheral blood mononuclear cells) of a patient and treated ex vivo in order to alter their production of transcription factors, enzymes, cytokines, lymphokines, or immunomodulatory molecules, before administering to a patient. Dendritic cells are highly potent APCs (Banchereau and Steinman, Nature 392:245-251, 1998). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within an immunogenic composition (see Zitvo-gel et al., Nature Med. 4:594-600, 1998). Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNF.alpha. to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNF|→, CD40 ligand, LPS, flt3 ligand and/or other compound(s) that induce differentiation, maturation and proliferation of dendritic cells.

The citrullinated peptides of the invention are arthritogenic and thus evoke an inflammatory response leading to RA. As such, these peptides can be used to induce clinical arthritis in non-human mammalians in order to provide an animal model for which novel pharmaceuticals may be tested and identified effective for the treatment of RA. Any animal that is transgenic for a MHC class II molecule that contains the shared epitope may be used within the scope of the present invention. In one aspect of the invention, the administration of one or more of the citrullinated peptides of the invention may be provided to HLA-DRB1*401 transgenic mice (DR4-IE tg) leading to the development of arthritic signs and eventual disease patterns of arthritis, more particularly rheumatoid arthritis. These DR4-IE tg transgenic mice express a chimeric MHC class II molecule that is composed of the human antigen binding domains (α1 and β1) and mouse CD4 binding domains (α2 and β2). The chimeric DR4 presents peptides in an identical manner as full human DR4 and these mice do not express endogenous MHC class II molecules. Further, these mice contain the same complement of B and T cells as wild-type mice and thus these transgenic mice are ideal for testing the immune response of SE restricted T cells in vivo and thus for identifying pharmaceutical agents that may decrease or prevent a T cell response leading to inflammation. While DR4-IE tg mice were used, it is understood that any mouse strain that is transgenic for a MHC class II molecules that contains the shared epitope may be used as an animal model for the testing of pharmaceutical compounds in the present invention.

The transgenic mice may be injected subcutaneously with a citrullinated protein containing one or more peptides of the invention (as well as any adjuvants or other pharmaceutical excipients and allowed to develop arthritic signs. In one aspect, full length citrullinated vimentin or citrullinated fibrinogen are administered to the transgenic mice to induce the development of arthritis. Potential pharmaceutical agents may be co-administered with the peptides or later once an inflammatory reaction is established to treat arthritis and to study the effect of these pharmaceutical actives upon the arthritic development. Preferably mice are used as animal model for arthritis, especially rheumatoid arthritis.

With the knowledge that the citrullinated peptides of the invention are arthritogenic and act via binding to MHC class II molecules with the shared epitope to evoke a T cell response leading to RA, diagnostic and therapeutic methods are now available for RA.

In one embodiment, the present invention may be used to detect autoreactive T cells from patients with RA or those suspected or predisposed to developing RA. A number of methods may be used to detect either T cells specific for the citrullinated peptide-MHC complex or detecting the presence of the citrullinated peptide-MHC complex itself. For example, a T cell proliferation assay known to those of skill in the art may be used to detect T cell activation in a subject peripheral blood mononuclear blood (PBMC) sample. Such method is conducted by the incorporation of a radioisotope such as for example $^3$H-thymidine as a measure of T cell proliferation (see Example section). Autoreactive T cell activity present in the PBMC can also be detected by measuring the cytokine release after activation by the citrullinated peptide-MHC class II complexes with cytokine-specific ELISA (i.e. ELISPOT). Another detection method is the measurement of expression of activation markers by FACS analysis, for example of Il-2R. Furthermore, soluble MHC class II molecules may be linked to a fluorochrome or liposome with bound citrullinated peptide and used to detect T cells which possess T cell receptors that recognize these complexes.

Monoclonal antibodies that recognize the citrullinated peptides may also be made and used to detect the presence of the peptide as presented/bound to MHC class II molecules having a shared epitope on antigen presenting cells (APC). This provides a rapid and simple method of diagnosis of disease as well as the disposition to developing RA. In general, methods for the preparation of antibodies are well known. In order to prepare polyclonal antibodies that would recognize the peptides of the invention, fusion proteins containing defined portions or all of vimentin or fibrinogen proteins or any of their alternative transcripts can be synthesized in bacteria by expression of corresponding DNA sequences in a suitable cloning vehicle. The protein can then be purified, coupled to a carrier protein and mixed with Freund's adjuvant (to help stimulate the antigenic response by the rabbits) and injected into rabbits or other laboratory animals. Alternatively, protein can be isolated from cultured cells expressing the protein. Following booster injections at bi-weekly intervals, the rabbits or other laboratory animals are then bled and the sera isolated. The sera can be used directly or purified prior to use, by affinity chromatography. The sera can then be used to probe protein extracts run on a polyacrylamide gel to identify the vimentin or fibrinogen protein, alternative transcript or any mutant thereof. Alternatively, synthetic peptides (as discussed above) can be made to the antigenic portions of these proteins and used to innoculate the animals.

Methods to produce monoclonal antibodies which specifically recognize mammalian or other species of vimentin and fibrinogen proteins or portions thereof, are known in the art. In general, cells actively expressing the protein are cultured or isolated from tissues and the cell extracts isolated. The extracts or recombinant protein extracts, containing the vimentin or fibrinogen protein, are injected in Freund's adjuvant into mice. After being injected 9 times over a three week period, the mice spleens are removed and resuspended in phosphate buffered saline (PBS). The spleen cells serve as a source of lymphocytes, some of which are producing antibody of the appropriate specificity. These are then fused with a permanently growing myeloma partner cell, and the products of the fusion are plated into a number of tissue culture wells in the presence of a selective agent such as HAT. The wells are then screened to identify those containing cells making useful antibody by ELISA. These are then freshly plated. After a period of growth, these wells are again screened to identify antibody-producing cells. Several cloning procedures are carried out until over 90% of the wells contain single clones which are positive for antibody production. From this procedure a stable lines of clones is established which produce the antibody. The monoclonal antibody can then be purified by affinity chromatography using Protein A or Protein G Sepharose.

Antibodies can also be made directed to the peptide/MHC Class II complex. Methods to generate such antibodies to the peptide/MHC Class II complex are known and described (i.e. Baeten, D., Steenbakkers PGA., Rovers E., Veys E M., Rijnders A M W., Meijerink J., Keyser F De and Boots A. Localisation of MHC Class II/HC gp-39 complexes in synovia of rheumatoid arthritis patients using complex-specific monoclonal antibodies. Abstracts of the 23$^{rd}$ European Workshop for Rheumatology Research, Vol 5 Suppl 1, February 2003; Baeten D., Steenbakkers P., Boots A., Veys E M., and Keyser, Fde., The presentation of the immunodominant epitope of HC gp-39 in the context of the RA-associated HLA class II molecules is specific for RA synovium. Abstracts of the 23$^{rd}$ European Workshop for Rheumatology Research, Vol 5 Suppl 1, February 2003).

A diagnostic composition comprising one or more of the peptides according to the invention and a suitable detecting agent thus forms part of the invention. Depending on the type of detection, the detection agent can be a radioisotope, an enzyme, or antibodies specific for cell surface or activation markers.

Also within the scope of the invention are test kits which comprise one or more peptides according to the invention. These test kits are suitable for use in a diagnostic method according to the invention.

The invention also encompasses therapeutic strategies that involve targeting the T cells that are specific for the citrullinated peptide/MHC class II complexes or disrupting the formation of these complexes. These methods may be used in combination with other known therapies for treating RA. For example, the activated T cells may be eliminated by inducing apoptosis of these cells which can be accomplished by administering soluble peptide-MHC class II complexes to a patient (i.e. U.S. Pat. No. 5,734,02, 6,106,840, 5,635,363, 6,211,342, U.S. patent application 20020176864 and 20020122818, the disclosures of which are incorporated herein in their entirety). The invention also encompasses the use of the peptides of the invention in therapeutic strategies using methods of RNA interference to modulate T cell activity in a subject. RNA interference ($RNA_i$) is a form of gene silencing triggered by double-stranded RNA (dsRNA). In one aspect of the invention using such a method, the peptides of the invention are combined with RNA sequences encoding for example a cytokine that will effect an APC (i.e. dendritic cells) which in turn will affect T cells to shift from an activated inflammatory response to one of a regulatory response. Different methods of RNA interference are described in Tuschl et al., Genes and Development 13:3191-3197, 1999; Fire et al., Nature, 1998, 391:806-811; and Zamore, Cell 101:25-33, 2000; and Applicant's Canadian Patent Application 2,388,441 (the disclosures of which are incorporated herein in their entirety).

The invention also encompasses methods of treatment of an autoimmune disorder such as Rheumatoid Arthritis by the administration of a therapeutic composition comprising one or more peptides according to the invention and a pharmaceutically acceptable carrier to induce systemic immunological tolerance. The induced tolerance leads to a reduction of the local inflammatory response in the tissue under attack. In one aspect the peptides can are administered via the mucosal epithelium of patients to induce such systemic immunological tolerance as method is disclosed for example in U.S. Pat. No. 5,843,445 (the disclosure of which is herein incorporated by reference in its entirety).

In another aspect of the invention, antibodies specific for citrullinated peptide/MHC class II complexes can be used to bind to the complex and thus prevent complex recognition by T cells (i.e. WO 02/14870). Alternatively, the peptide binding groove of the MHC class II molecules may be bound with a high affinity non citrullinated peptide that is not then recognized by the T cell or that is bound by an antibody thus preventing the formation of citrullated peptide/MHC class II complexes (i.e. U.S. Pat. No. 6,355,617). Alternatively, the modification of certain peptides having arginine to that of citrulline may be prevented by the use of inhibitors to the enzyme peptidylarginine deiminase that catalyzes this amino acid reaction.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Methods of synthetic chemistry, protein and peptide biochemistry, molecular biology, pharmacology and immunology referred to but not explicitly described in this disclosure and examples are reported in the scientific literature and are well known to those skilled in the art.

Animals

HLA-DR4-IE transgenic, murine MHC class II deficient mice were used in these experiments (Ito K, Bian H J, Molina M, Han J, Magram J, Saar E, Belunis C, Bolin D R, Arceo R, Campbell R, Falcioni F, Vidovic D, Hammer J, Nagy Z A. 1996. HLA-DR4-IE chimeric class II transgenic, murine class II-deficient mice are susceptible to experimental allergic encephalomyelitis. *J. Exp. Med.* 183:2635). These mice were bred and maintained as previously described (Hill, J. A., Wang, D., Jevnikar, A. M., Cairns, E., Bell, D. A. 2002. The relationship between predicted peptide-MHC class II affinity and T cell activation in a HLA-DRβ1*0401 MHC class II mouse model. *Arthritis Res.* 5:R40).

Peptides

Peptides used in these studies were synthesized and purified by the manufacturer (Genemed Synthesis, San Francisco, Calif.). Peptides were selected based on their predicted affinity for DRB1*0401 according to the method of Hammer et al (Hammer J, Bono E, Gallazzi F, Belunis C, Nagy Z, Sinigaglia F. 1994. Precise prediction of major histocompatibility complex class II-peptide interaction based on peptide side chain scanning *J. Exp. Med.* 180:2353). Underlined amino acids indicate the residues interacting with the nine MHC class II binding pockets (P1-P9), while those that appear in bold interact at the P4 shared epitope position. The sequences of the peptides used from the proteoglycan aggrecan are as follows: P4D=human aggrecan peptide 280-292, AG WLADRSVRYPI (SEQ ID NO. 38); P4R=altered human aggrecan peptide 280-292, AGWLARRSVRYPI (SEQ ID NO. 39); P4Cit=altered human aggrecan peptide 280-292, AGWLACitRSVRYPI (SEQ ID NO. 40). Since citrulline is not accounted for in the predictive algorithm of Hammer et al. the value of glutamine was substituted for arginine when identifying a candidate T cell epitope from vimentin (glutamine has the same terminal side-chain group as citrulline). The sequences of the vimentin peptides used are as follows: Vim 65-77=human vimentin peptide 65-77, SA VRARSSVPGVR (SEQ ID NO. 41), Vim R70Cit=altered human vimentin peptide 65-77, SAVRACitSSVPGVR (SEQ ID NO. 1).

Immunizations

DR4 tg mice were immunized intradermally at the interior side of both hind legs with 100 μl of peptide (1 μg/μl) emulsified in CFA (Difco Laboratories, Detroit, Mich.) in a 1:1 volume ratio. After 10 days, mice were sacrificed and their draining lymph nodes were removed for in vitro proliferation and cytokine assays.

T Cell Cultures

Cell suspensions were prepared from the draining lymph nodes and cultured in 96-well plates at a concentration of $4 \times 10^5$ cells/well in the presence or absence of peptide antigen for 4 days. Anti-DR antibody (B D PharMingen, Mississauga, O N) was added to some cultures (1 μg/ml) to confirm DR restricted T cell responses as described previously (Andersson E C, Hansen B E, Jacobsen H, Madsen L S, Andersen C B, Engberg J, Rothbard J B, McDevitt G S, Malmstrom V, Holmdahl R, Svejgaard A, Fugger L. 1998. Definition of MHC and T cell receptor contacts in the HLA-DR4 restricted immunodominant epitope in type II collagen and characterization of collagen-induced arthritis in HLA-DR4 and human CD4 transgenic mice. *Proc. Natl. Acad. Sci. USA*. 95:7574). Culture supernatants were removed after 78 hrs to test IFN-γ production by ELISA (B D PharMingen, Mississauga, O N) as described previously (Hill, J. A., Wang, D., Jevnikar, A. M., Cairns, E., Bell, D. A. 2002. The relationship between predicted peptide-MHC class II affinity and T cell activation in a HLA-DRβ1*0401 MHC class II mouse model. *Arthritis Res.* 5:R40). Cytokine production was measured in duplicate and represents the average antigen specific cytokine production (cytokine production in control samples+2 SD were subtracted from the peptide specific cytokine production)±SD. Eighteen hours before culture termination, 1 μCi of [$^3$H] thymidine (ICN Biomedicals, Montreal, PQ) was added to each well to assess T cell proliferation. Proliferation experiments were conducted in triplicate and results are presented as average proliferation in cpm±SD or stimulation index (cpm of experimental sample/cpm of control sample)±SEM.

Peptide-Binding Assay

Peptide binding affinity to purified HLA-DRB1*0101, *0401, *0404, *0301, *0701, *0802, *1101, and *1302 molecules was determined relative to radio-labelled peptide probes as described previously (Southwood S, Sidney J, Kondo A, del Guercio M F, Appella E, Hoffman S, Kubo R T, Chesnut R W, Grey H M, Sette A. 1998. Several common HLA-DR types share largely overlapping peptide binding repertoires. *J. Immunol.* 160:3363). The nM concentration of unlabelled vimentin peptide necessary for 50% inhibition of the labelled peptide to the purified HLA-DRB1 molecules ($IC_{50}$) was used as an approximation of the affinity of interaction (kDa). Results are expressed as the inverse of the $IC_{50}$ values measured in nM.

Although preferred embodiments of the invention have been described herein in detail, it will be understood by those skilled in the art that variations may be made thereto without departing from the spirit of the invention or the scope of the appended claims.

The invention claimed is:

1. An isolated citrullinated peptide, said peptide binding with a high or increased affinity to a MHC class II molecule having the shared epitope compared with a non-citrullinated peptide, wherein said binding to said shared epitope evokes a T cell response in the blood of a patient with an autoimmune disorder, and wherein said peptide comprises SAVRACitSS-VPGVR (SEQ ID NO. 1) and is up to 55 amino acids in length.

2. The peptide of claim 1, wherein said citrullinated peptide is produced by the action of peptidylarginine deiminase on an endogenous or exogenous protein that contains at least one arginine.

3. The peptide of claim 1, wherein said autoimmune disorder is rheumatoid arthritis.

4. The peptide of claim 1, wherein said T cell is a CD4+ T cell.

5. A pharmaceutical composition comprising an effective amount of the peptide of claim 1, and a pharmaceutically acceptable carrier.

6. A test kit for the detection of activated autoreactive T cells which are reactive with a citrullinated peptide antigen bound to an MHC class II shared epitope positive cell, said test kit comprising the peptide of claim 1.

* * * * *

UNITED STATES PATENT AND TRADEMARK OFFICE
CERTIFICATE OF CORRECTION

PATENT NO. : 8,198,401 B2
APPLICATION NO. : 10/794227
DATED : June 12, 2012
INVENTOR(S) : Hill et al.

Page 1 of 1

It is certified that error appears in the above-identified patent and that said Letters Patent is hereby corrected as shown below:

At column 2, line 51, please delete "Pemeger" and insert --Perneger--, therefor.

At column 9, line 39, please delete "Stem" and insert --Stern--, therefor.

At column 9, line 55, please delete "I-peptide" and insert --II-peptide--, therefor.

At column 15, line 27, please delete "Technology" and insert --Technology:--, therefor.

At column 21, line 40 (Approx.), please delete "DRBI *0401" and insert --DRB1*0401--, therefor.

Signed and Sealed this
Twenty-seventh Day of November, 2012

David J. Kappos
*Director of the United States Patent and Trademark Office*

SEQUENCE LISTING

<160> NUMBER OF SEQ ID NOS: 41

<210> SEQ ID NO 1
<211> LENGTH: 13
<212> TYPE: PRT

```
<213> ORGANISM: Artificial Sequence
<220> FEATURE:
<223> OTHER INFORMATION: Chemically synthesized citrullinated peptide
      derived from human vimentin fragment 65-77 with a single amino
      acid substitution at position 70
<220> FEATURE:
<221> NAME/KEY: VARIANT
<222> LOCATION: 6
<223> OTHER INFORMATION: Xaa is citrulline

<400> SEQUENCE: 1

Ser Ala Val Arg Ala Xaa Ser Ser Val Pro Gly Val Arg
 1               5                  10

<210> SEQ ID NO 2
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 2-10 with a single
      amino acid substitution at position 5
<220> FEATURE:
<221> NAME/KEY: VARIANT
<222> LOCATION: 4
<223> OTHER INFORMATION: Xaa is citrulline

<400> SEQUENCE: 2

Phe Ser Met Xaa Ile Val Cys Leu Val
 1               5

<210> SEQ ID NO 3
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 39-47 with a single
      amino acid substitution at position 42
<220> FEATURE:
<221> NAME/KEY: VARIANT
<222> LOCATION: 4
<223> OTHER INFORMATION: Xaa is citrulline

<400> SEQUENCE: 3

Val Val Glu Xaa His Gln Ser Ala Cys
 1               5

<210> SEQ ID NO 4
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 81-89 with a single
      amino acid substitution at position 84
<220> FEATURE:
<221> NAME/KEY: VARIANT
<222> LOCATION: 4
<223> OTHER INFORMATION: Xaa is citrulline

<400> SEQUENCE: 4

Phe Thr Asn Xaa Ile Asn Lys Leu Lys
 1               5

<210> SEQ ID NO 5
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 134-142 with a
```

-continued single amino acid substitution at position 137
<220> FEATURE:
<221> NAME/KEY: VARIANT
<222> LOCATION: 4
<223> OTHER INFORMATION: Xaa is citrulline

<400> SEQUENCE: 5

Leu Arg Ser Xaa Ile Glu Val Leu Lys
 1               5

<210> SEQ ID NO 6
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 140-148 with a
      single amino acid substitution at position 143
<220> FEATURE:
<221> NAME/KEY: VARIANT
<222> LOCATION: 4
<223> OTHER INFORMATION: Xaa is citrulline

<400> SEQUENCE: 6

Val Leu Lys Xaa Lys Val Ile Glu Lys
 1               5

<210> SEQ ID NO 7
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 175-183 with a
      single amino acid substitution at position 178
<220> FEATURE:
<221> NAME/KEY: VARIANT
<222> LOCATION: 4
<223> OTHER INFORMATION: Xaa is citrulline

<400> SEQUENCE: 7

Ile Lys Ile Xaa Ser Cys Arg Gly Ser
 1               5

<210> SEQ ID NO 8
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 213-221 with a
      single amino acid substitution at position 216
<220> FEATURE:
<221> NAME/KEY: VARIANT
<222> LOCATION: 4
<223> OTHER INFORMATION: Xaa is citrulline

<400> SEQUENCE: 8

Leu Pro Ser Xaa Asp Arg Gln His Leu
 1               5

<210> SEQ ID NO 9
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 509-517 with a
      single amino acid substitution at position 512
<220> FEATURE:
<221> NAME/KEY: VARIANT
<222> LOCATION: 4

-continued

<223> OTHER INFORMATION: Xaa is citrulline

<400> SEQUENCE: 9

Phe Arg His Xaa His Pro Asp Glu Ala
 1               5

<210> SEQ ID NO 10
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 570-578 with a
      single amino acid substitution at position 573
<220> FEATURE:
<221> NAME/KEY: VARIANT
<222> LOCATION: 4
<223> OTHER INFORMATION: Xaa is citrulline

<400> SEQUENCE: 10

Phe Pro Ser Xaa Gly Lys Ser Ser Ser
 1               5

<210> SEQ ID NO 11
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 675-683 with a
      single amino acid substitution at position 678
<220> FEATURE:
<221> NAME/KEY: VARIANT
<222> LOCATION: 4
<223> OTHER INFORMATION: Xaa is citrulline

<400> SEQUENCE: 11

Ile Gln Gln Xaa Met Asp Gly Ser Leu
 1               5

<210> SEQ ID NO 12
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 717-725 with a
      single amino acid substitution at position 720
<220> FEATURE:
<221> NAME/KEY: VARIANT
<222> LOCATION: 4
<223> OTHER INFORMATION: Xaa is citrulline

<400> SEQUENCE: 12

Leu Thr Gln Xaa Gly Ser Val Leu Arg
 1               5

<210> SEQ ID NO 13
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 740-748 with a
      single amino acid substitution at position 743
<220> FEATURE:
<221> NAME/KEY: VARIANT
<222> LOCATION: 4
<223> OTHER INFORMATION: Xaa is citrulline

<400> SEQUENCE: 13

Tyr His Phe Xaa Val Gly Ser Glu Ala
1               5

<210> SEQ ID NO 14
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 827-835 with a
      single amino acid substitution at position 830
<220> FEATURE:
<221> NAME/KEY: VARIANT
<222> LOCATION: 4
<223> OTHER INFORMATION: Xaa can be any naturally occurring amino acid

<400> SEQUENCE: 14

Tyr Asp Pro Xaa Asn Asn Ser Pro Tyr
1               5

<210> SEQ ID NO 15
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 844-852 with a
      single amino acid substitution at position 847
<220> FEATURE:
<221> NAME/KEY: VARIANT
<222> LOCATION: 4
<223> OTHER INFORMATION: Xaa is citrulline

<400> SEQUENCE: 15

Val Ser Phe Xaa Gly Ala Asp Tyr Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 851-859 with a
      single amino acid substitution at position 854
<220> FEATURE:
<221> NAME/KEY: VARIANT
<222> LOCATION: 4
<223> OTHER INFORMATION: Xaa is citrulline

<400> SEQUENCE: 16

Tyr Ser Leu Xaa Ala Val Arg Met Lys
1               5

<210> SEQ ID NO 17
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen alpha fragment 858-866 with a
      single amino acid substitution at position 861
<220> FEATURE:
<221> NAME/KEY: VARIANT
<222> LOCATION: 4
<223> OTHER INFORMATION: Xaa is citrulline

<400> SEQUENCE: 17

Met Lys Ile Xaa Pro Leu Val Thr Gln
1               5

```
<210> SEQ ID NO 18
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen beta fragment 71-79 with a single
      amino acid substitution at position 74
<220> FEATURE:
<221> NAME/KEY: VARIANT
<222> LOCATION: 4
<223> OTHER INFORMATION: Xaa is citrulline

<400> SEQUENCE: 18

Tyr Arg Ala Xaa Pro Ala Lys Ala Ala
1               5

<210> SEQ ID NO 19
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen beta fragment 155-163 with a single
      amino acid substitution at position 158
<220> FEATURE:
<221> NAME/KEY: VARIANT
<222> LOCATION: 4
<223> OTHER INFORMATION: Xaa is citrulline

<400> SEQUENCE: 19

Trp Gln Lys Xaa Gln Lys Gln Val Lys
1               5

<210> SEQ ID NO 20
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen beta fragment 282-290 with a single
      amino acid substitution at position 285
<220> FEATURE:
<221> NAME/KEY: VARIANT
<222> LOCATION: 4
<223> OTHER INFORMATION: Xaa is citrulline

<400> SEQUENCE: 20

Ile Gln Asn Xaa Gln Asp Gly Ser Val
1               5

<210> SEQ ID NO 21
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen beta fragment 433-441 with a single
      amino acid substitution at position 436
<220> FEATURE:
<221> NAME/KEY: VARIANT
<222> LOCATION: 4
<223> OTHER INFORMATION: Xaa is citrulline

<400> SEQUENCE: 21

Trp Tyr Asn Xaa Cys His Ala Ala Asn
1               5

<210> SEQ ID NO 22
<211> LENGTH: 9
<212> TYPE: PRT
<213> ORGANISM: Artificial Sequence
```

```
<220> FEATURE:
<223> OTHER INFORMATION: Chemically synthesized citrullinated peptide
      derived from human fibrinogen beta fragment 475-483 with a single
      amino acid substitution at position 478
<220> FEATURE:
<221> NAME/KEY: VARIANT
<222> LOCATION: 4
<223> OTHER INFORMATION: Xaa is citrulline

<400> SEQUENCE: 22

Tyr Ser Met Xaa Lys Met Ser Met Lys
1               5

<210> SEQ ID NO 23
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen beta fragment 482-490 with a single
      amino acid substitution at position 485
<220> FEATURE:
<221> NAME/KEY: VARIANT
<222> LOCATION: 4
<223> OTHER INFORMATION: Xaa is citrulline

<400> SEQUENCE: 23

Met Lys Ile Xaa Pro Phe Phe Pro Gln
1               5

<210> SEQ ID NO 24
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen gamma fragment 5-13 with a single
      amino acid substitution at position 8
<220> FEATURE:
<221> NAME/KEY: VARIANT
<222> LOCATION: 4
<223> OTHER INFORMATION: Xaa is citrulline

<400> SEQUENCE: 24

Leu His Pro Xaa Asn Leu Ile Leu Tyr
1               5

<210> SEQ ID NO 25
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen gamma fragment 28-36 with a single
      amino acid substitution at position 31
<220> FEATURE:
<221> NAME/KEY: VARIANT
<222> LOCATION: 4
<223> OTHER INFORMATION: Xaa is citrulline

<400> SEQUENCE: 25

Val Ala Thr Xaa Asp Asn Cys Cys Ile
1               5

<210> SEQ ID NO 26
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen gamma fragment 37-45 with a single
      amino acid substitution at position 40
```

-continued

```
<220> FEATURE:
<221> NAME/KEY: VARIANT
<222> LOCATION: 4
<223> OTHER INFORMATION: Xaa is citrulline

<400> SEQUENCE: 26

Leu Asp Glu Xaa Phe Gly Ser Tyr Cys
 1               5

<210> SEQ ID NO 27
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen gamma fragment 110-118 with a
      single amino acid substitution at position 113
<220> FEATURE:
<221> NAME/KEY: VARIANT
<222> LOCATION: 4
<223> OTHER INFORMATION: Xaa is citrulline

<400> SEQUENCE: 27

Leu Lys Ser Xaa Ile Met Leu Glu Glu
 1               5

<210> SEQ ID NO 28
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen gamma fragment 220-228 with a
      single amino acid substitution at position 223
<220> FEATURE:
<221> NAME/KEY: VARIANT
<222> LOCATION: 4
<223> OTHER INFORMATION: Xaa is citrulline

<400> SEQUENCE: 28

Phe Gln Lys Xaa Leu Asp Gly Ser Val
 1               5

<210> SEQ ID NO 29
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen gamma fragment 270-278 with a
      single amino acid substitution at position 273
<220> FEATURE:
<221> NAME/KEY: VARIANT
<222> LOCATION: 4
<223> OTHER INFORMATION: Xaa is citrulline

<400> SEQUENCE: 29

Tyr Ala Leu Xaa Val Glu Leu Glu Asp
 1               5

<210> SEQ ID NO 30
<211> LENGTH: 8
<212> TYPE: PRT
<213> ORGANISM: Artificial Sequence
<220> FEATURE:
<223> OTHER INFORMATION: Chemically synthesized citrullinated peptide
      derived from human fibrinogen gamma fragment 279-286 with a
      single amino acid substitution at position 282
<220> FEATURE:
<221> NAME/KEY: VARIANT
<222> LOCATION: 4
<223> OTHER INFORMATION: Xaa is citrulline
```

```
<400> SEQUENCE: 30

Trp Asn Gly Xaa Thr Ser Thr Ala
 1               5

<210> SEQ ID NO 31
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human fibrinogen gamma fragment 398-406 with a
      single amino acid substitution at position 401
<220> FEATURE:
<221> NAME/KEY: VARIANT
<222> LOCATION: 4
<223> OTHER INFORMATION: Xaa is citrulline

<400> SEQUENCE: 31

Trp Lys Thr Xaa Trp Tyr Ser Met Lys
 1               5

<210> SEQ ID NO 32
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human vimentin fragment 61-69 with a single amino
      acid substitution at position 64
<220> FEATURE:
<221> NAME/KEY: VARIANT
<222> LOCATION: 4
<223> OTHER INFORMATION: Xaa is citrulline

<400> SEQUENCE: 32

Tyr Ala Thr Xaa Ser Ser Ala Val Arg
 1               5

<210> SEQ ID NO 33
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human vimentin fragment 68-76 with a single amino
      acid
      substitution at position 71
<220> FEATURE:
<221> NAME/KEY: VARIANT
<222> LOCATION: 4
<223> OTHER INFORMATION: Xaa can be any naturally occurring amino acid

<400> SEQUENCE: 33

Val Arg Leu Xaa Ser Ser Val Pro Gly
 1               5

<210> SEQ ID NO 34
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human vimentin fragment 115-123 with a single amino
      acid substitution at position 118
<220> FEATURE:
<221> NAME/KEY: VARIANT
<222> LOCATION: 4
<223> OTHER INFORMATION: Xaa is citrulline

<400> SEQUENCE: 34
```

Leu Asn Asp Xaa Phe Ala Asn Tyr Ile
1               5

<210> SEQ ID NO 35
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human vimentin fragment 193-201 with a single amino
      acid substitution at position 196
<220> FEATURE:
<221> NAME/KEY: VARIANT
<222> LOCATION: 4
<223> OTHER INFORMATION: Xaa is citrulline

<400> SEQUENCE: 35

Met Leu Gln Xaa Glu Glu Ala Glu Asn
1               5

<210> SEQ ID NO 36
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human vimentin fragment 421-429 with a single amino
      acid substitution at position 424
<220> FEATURE:
<221> NAME/KEY: VARIANT
<222> LOCATION: 4
<223> OTHER INFORMATION: Xaa is citrulline

<400> SEQUENCE: 36

Leu Asn Leu Xaa Glu Thr Asn Leu Asp
1               5

<210> SEQ ID NO 37
<211> LENGTH: 9
<212> TYPE: PRT
<213> ORGANISM: Artificial Sequence
<220> FEATURE:
<223> OTHER INFORMATION: Chemically synthesized citrullinated peptide
      derived from human vimentin fragment 447-455 with a single amino
      acid substitution at position 450
<220> FEATURE:
<221> NAME/KEY: VARIANT
<222> LOCATION: 4
<223> OTHER INFORMATION: Xaa is citrulline

<400> SEQUENCE: 37

Val Glu Thr Xaa Asp Gly Gln Val Ile
1               5

<210> SEQ ID NO 38
<211> LENGTH: 13
<212> TYPE: PRT
<213> ORGANISM: Artificial Sequence
<220> FEATURE:
<223> OTHER INFORMATION: Chemically synthesized peptide derived from
      human aggrecan fragment 299-311

<400> SEQUENCE: 38

Ala Gly Trp Leu Ala Asp Arg Ser Val Arg Tyr Pro Ile
1               5                   10

<210> SEQ ID NO 39
<211> LENGTH: 13
<212> TYPE: PRT
<213> ORGANISM: Artificial Sequence
<220> FEATURE:

```
<223> OTHER INFORMATION: Chemically synthesized peptide derived from
      human aggrecan fragment 299-311 with a single amino acid
      substitution at position 304

<400> SEQUENCE: 39

Ala Gly Trp Leu Ala Arg Arg Ser Val Arg Tyr Pro Ile
 1               5                   10

<210> SEQ ID NO 40
<211> LENGTH: 13
<212> TYPE: PRT
<213> ORGANISM: Artificial Sequence
<220> FEATURE:
<223> OTHER INFORMATION: Chemically synthesized citrullinated peptide
      derived from human aggrecan fragment 299-311 with a single amino
      acid substitution at position 304
<220> FEATURE:
<221> NAME/KEY: VARIANT
<222> LOCATION: 6
<223> OTHER INFORMATION: Xaa is citrulline

<400> SEQUENCE: 40

Ala Gly Trp Leu Ala Xaa Arg Ser Val Arg Tyr Pro Ile
 1               5                   10

<210> SEQ ID NO 41
<211> LENGTH: 13
<212> TYPE: PRT
<213> ORGANISM: Homo sapiens
<220> FEATURE:
<223> OTHER INFORMATION: Chemically synthesized human vimentin peptide
      fragment derived from amino acids 65-77

<400> SEQUENCE: 41

Ser Ala Val Arg Ala Arg Ser Ser Val Pro Gly Val Arg
 1               5                   10
```